(12) United States Patent
Knight

(10) Patent No.: US 9,919,162 B2
(45) Date of Patent: Mar. 20, 2018

(54) APPARATUS FOR PROVIDING LIGHT THERAPY

(71) Applicant: Blu Room Enterprises, LLC, Yelm, WA (US)

(72) Inventor: Judith Darlene Knight, Yelm, WA (US)

(73) Assignee: Blu Room Enterprises, LLC, Yelm, WA (US)

( * ) Notice: Subject to any disclaimer, the term of this patent is extended or adjusted under 35 U.S.C. 154(b) by 0 days.

(21) Appl. No.: 14/861,915

(22) Filed: Sep. 22, 2015

(65) Prior Publication Data

US 2017/0080246 A1    Mar. 23, 2017

(51) Int. Cl.
*A61N 5/06* (2006.01)
*A61M 21/02* (2006.01)
(Continued)

(52) U.S. Cl.
CPC .............. *A61N 5/06* (2013.01); *A61G 10/02* (2013.01); *A61M 21/02* (2013.01);
(Continued)

(58) Field of Classification Search
CPC .............................. A61M 21/00–21/02; A61M 2021/0005–2021/0088;
(Continued)

(56) References Cited

U.S. PATENT DOCUMENTS 3,643,941 A    2/1972 Kashar
3,703,173 A    11/1972 Dixon
(Continued)

FOREIGN PATENT DOCUMENTS

CN    203564634 U    4/2014
EP    2799104 A1    11/2014
WO    2001/045780    6/2001

OTHER PUBLICATIONS

Mindset Hypnosis & Health, "Light and Sound Therapy," https://mindsethypnosis.com/LightSound_Therapy.html. Accessed on Jul. 15, 2015 (2 pages).

(Continued)

*Primary Examiner* — Catherine B Kuhlman
(74) *Attorney, Agent, or Firm* — John W. Branch; Lowe Graham Jones PLLC

(57) ABSTRACT

Methods and apparatuses for providing therapy, including light therapy, to a user positioned within an enclosure are described herein. A method includes generating and selecting therapy settings based on user information and positioning the user within an enclosure having a plurality of light sources. The enclosure is configured to focus light on the user at a location within the enclosure according to selected settings. Post-therapy user information is provided to generate a report regarding the user and may include the user's measured physical attributes, measured spectrum values, reported information, or survey information. Aromatherapy, audio therapy, or air therapy may be additionally provided. An apparatus includes an enclosure with a control system configured to perform a therapy method. An enclosure may be have the shape of an octagon or another shape. A computer readable non-transitory storage media includes instructions for providing therapy to a user positioned within the enclosure.

20 Claims, 18 Drawing Sheets

(51) Int. Cl.
*A61G 10/02* (2006.01)
*A61M 21/00* (2006.01)

(52) U.S. Cl.
CPC ......... *A61N 5/0613* (2013.01); *A61N 5/0624* (2013.01); *A61M 2021/005* (2013.01); *A61M 2021/0016* (2013.01); *A61M 2021/0027* (2013.01); *A61M 2021/0033* (2013.01); *A61M 2021/0038* (2013.01); *A61M 2021/0044* (2013.01); *A61M 2021/0066* (2013.01); *A61M 2205/052* (2013.01); *A61M 2205/053* (2013.01); *A61M 2205/058* (2013.01); *A61M 2205/502* (2013.01); *A61N 2005/0626* (2013.01); *A61N 2005/0632* (2013.01); *A61N 2005/0637* (2013.01); *A61N 2005/0661* (2013.01); *A61N 2005/0663* (2013.01)

(58) Field of Classification Search
CPC ...... A61G 10/00–10/04; A61G 11/00–11/009; A61N 5/0613–5/0625; A61N 2005/0636–2005/0641; A61N 2005/0666
USPC ...................................... 607/88–95
See application file for complete search history.

(56) References Cited

U.S. PATENT DOCUMENTS

| | | | |
|---|---|---|---|
| 3,773,049 A | 11/1973 | Rabichev et al. | |
| 3,826,250 A | 7/1974 | Adams | |
| 4,103,175 A * | 7/1978 | Levin | A61N 5/0614 250/503.1 |
| 4,506,511 A | 3/1985 | Cameto et al. | |
| 4,640,266 A | 2/1987 | Levy | |
| 4,974,922 A * | 12/1990 | Mori | A61N 5/06 385/147 |
| 5,245,998 A | 9/1993 | Sundsrud et al. | |
| 5,495,857 A | 3/1996 | Fegan | |
| 5,601,619 A * | 2/1997 | Drechsler | A61N 5/0614 607/88 |
| 5,645,578 A | 7/1997 | Daffer et al. | |
| 5,676,633 A | 10/1997 | August | |
| 5,681,259 A | 10/1997 | August | |
| 5,725,472 A | 3/1998 | Weathers | |
| 5,891,186 A | 4/1999 | Daffer et al. | |
| 6,497,231 B1 | 12/2002 | White | |
| 6,623,511 B1 | 9/2003 | Daffer et al. | |
| 7,108,654 B2 | 9/2006 | McNew | |
| 7,177,079 B2 | 2/2007 | Cromer et al. | |
| 7,201,766 B2 | 4/2007 | Butler | |
| 7,524,279 B2 | 4/2009 | Auphan | |
| 7,537,576 B1 | 5/2009 | Worley, III | |
| 7,578,783 B2 | 8/2009 | Klein | |
| 7,654,949 B2 | 2/2010 | McNew | |
| 7,846,084 B2 | 12/2010 | McNew | |
| 8,337,385 B1 | 12/2012 | Cornell | |
| 8,579,795 B2 | 11/2013 | Martel | |
| 2004/0030371 A1 | 2/2004 | Barghelame | |
| 2004/0261170 A1 | 12/2004 | Brunelle | |
| 2007/0287881 A1 | 12/2007 | Akimov et al. | |
| 2008/0077199 A1 * | 3/2008 | Shefi | A61N 5/0613 607/88 |
| 2009/0235447 A1 | 9/2009 | Zack et al. | |
| 2011/0063670 A1 * | 3/2011 | Ito | G06F 3/1204 358/1.15 |
| 2013/0172963 A1 * | 7/2013 | Moffat | A61N 5/0616 607/94 |
| 2013/0253621 A1 * | 9/2013 | DeLuca | A61N 5/0622 607/94 |
| 2014/0121453 A1 | 5/2014 | Maslowski et al. | |
| 2014/0276248 A1 * | 9/2014 | Hall | A61N 1/0432 601/2 |
| 2015/0141741 A1 | 5/2015 | Sullivan | |

OTHER PUBLICATIONS

Cantu, Carolyn, "White Space and Sensory Rooms," http://occupational-therapy.advanceweb.com/Article/White-Space-and-Sensory-Rooms.aspx. Sep. 20, 2004, Accessed Jul. 15, 2015 (2 pages).
Natural Rejuvenation, "Sound and Light Therapy," http://www.naturalrejuvenation.com/—Sound—Light-Therapy.html. Accessed Jul. 16, 2015 (4 pages).
Light and Sound Spa, "Chromatherapy and Light Therapy," http://www.lightandsoundspa.com/light—sound-therapy.html. Accessed Jul. 16, 2015 (2 pages).
McKusick, Eileen, "The Therapeutic Use of Sound in Alternative and Conventional Medicine," Foundation for Alternative and Integrative Medicine, http://www.faim.org/complementaryalternative/therapeutic-use-sound-alternative-conventional-medicine.html. Accessed Jul. 16, 2015 (8 pages).
International Search Report and Written Opinion for International Patent Application No. PCT/US2015/051540, dated Jun. 15, 2016, 14 pages.

* cited by examiner

APPARATUS FOR PROVIDING LIGHT THERAPY

TECHNICAL FIELD

The invention relates to methods and devices for promoting health in users by means of an enclosure that provides light therapy.

BACKGROUND

Modern science has provided increasing insight into the mental and physiological mechanisms of stress and its effects on human health. A wide variety of factors, including age, family dynamics, diet, exercise, work-related demands, environmental toxins, and genetics can contribute substantially to stress and an individual's ability to cope therewith. Stress is now understood as both a mental or psychological phenomenon and a physiological state, both of which relate to tension, wear, and strain on the individual and which cause a variety of ill effects, including heart disease, weight gain, cancer, and depression.

Accordingly, relaxation, or de-stressing, has increasingly been shown to have measurable health effects, ameliorating unhealthy conditions caused by stress and prolonging life. Relaxation may be promoted in a variety of ways, both at the decision making level of the individual—e.g., whether to take a vacation, to engage in mental therapy, or to choose a less stressful occupation—and at the molecular biological level.

Light has long been associated with causing healthful effects on biological systems. For example, the health-promoting properties of sunlight were accepted experiential knowledge in the ancient Egyptian and Greek cultures of Akhenaton and Herodotus. More recently, modern scientific research has shown that certain cellular activities may be modulated by exposure of the cellular tissue to light. Light of different energies (i.e., different wavelengths of light) can act on different mechanisms within individual cells within the cellular tissue to stimulate or suppress biological activity within the cells in a process commonly referred to as photobiomodulation. In certain photobiomodulation applications, commonly known as light therapy or phototherapy, the different wavelengths are used to promote healing, revitalize and rejuvenate cells, and in some circumstances, stimulate cellular regeneration and regrowth.

Biomolecules like cytochrome-C oxidase, hemoglobin, myoglobin, and nicotinamide adenine dinucleotide (NADH), found in cellular tissue, are recognized as photon acceptors and serve to initiate biochemical cellular response to photons. Additionally, it is recognized that certain biologic quantum field effects result from exposing cellular tissue to photonic light and that living cells generate low levels of photons, called biophotons. These biophotons are non-thermal in nature and are coupled to physiological functions in the cellular tissue. Biophotons represent regulatory activity from chemical reactivity within a cell and also perform regulatory activity over a given cellular tissue to promote cell growth and differentiation, and to provide intercellular and intracellular communication, such as for example, synchronicity in biofunction between cells. Such biophotons within a cellular tissue can be simulated by photonic light of one or more specific wavelengths from a source external to the cellular tissue. Such photonic light, when exposed to the cellular tissue, results in promotion of regulatory activity within the cells of the exposed cellular tissue.

Thus, it is generally accepted that cell activity can be up-regulated and down-regulated by specific wavelengths of low intensity light. The up- and down-regulation of cell activity through photobiomodulation is used to suppress cytokines, block the matrix metalloproteinases (MMP) cascade, suppress interleukins (IL) and tissue necrosis factors, and decrease inflammation of cellular tissue. Photobiomodulation is also used to affect mitochondrial density and activity, cell proliferation and adhesiveness, and DNA and RNA production. Phototherapy has been shown to affect vascular endothelial growth factor (VEGF) expression (both enhancement and suppression) and to protect against a wide variety of toxins, such as chemical, ionizing, and bacteriologic toxins.

At least some of the known effects of the various wavelengths on body tissues are as follows. Light in the yellow range (approximately 577 nm to 597 nm) has been shown to switch off collagenase production by down-regulating MMPs and switching on new collagen production. Collagenases are enzymes that break down the native collagen that holds animal tissue together. Thus, use of light in the yellow range for phototherapy ultimately results in increased cohesion of cells in animal tissue. Light in the red range (approximately 640 nm to 700 nm) has been shown to decrease inflammation in injured tissue, increase ATP production, and otherwise stimulate beneficial cellular activity. Light in the blue range (approximately 405 nm to 450 nm) has been shown to kill various microorganisms. For example, light in the blue range has been shown to kill the propionibacterium that causes acne by activating the porphyrins produced by the bacteria. Accordingly, phototherapy has been utilized to treat infants for jaundice, to treat acne and other skin conditions, to treat rhinitis, and to treat traumatic tissue injuries.

Thus, varying wavelengths of light along the visible light scale are known to have photobiomodulatory effects. Light with shorter wavelengths, such as visible blue light and ultraviolet (UV) light, is possessed of higher energy than light with longer wavelengths. UV light that reaches Earth includes the UVA (from about 320 nm to about 400 nm) and UVB (from about 290 nm to about 320 nm) forms. Like blue light and other visible-spectrum energies discussed above, UV light is known to play an important role in modulating biological processes. For example, the role of UVB light in producing non-dietary Vitamin D secosteroids—which are necessary for enhancing dietary absorption of minerals such as calcium, iron, magnesium, and zinc—is well known: UVB radiation converts the provitamin D7 (7-dehydrocholesterol) into pre-vitamin D3 in the outer dermis; the biologically inert pre-vitamin is hydrodxylated in the liver and kidney to produce Vitamin D3, which influences a variety of biological functions, including cellular information, cell differentiation, immune response, macrophage activity, and myocardial metabolism.

Exposure to UVB radiation is also important in maintaining the body's natural circadian rhythms. Metabolism, sleep, arousal, and feeding activities are known to be tied to the regular diurnal/nocturnal light cycle. Thus, UVB radiation may be applied to an affected user to correct aberrant circadian rhythms, improve mood and alleviate depression, raise metabolism, heal injuries such as muscle sprains or tendonitis, or to supplement abnormal production of vitamin D from dietary sources, such as in users afflicted with cystic fibrosis or short bowel syndrome. Therefore, high-energy lights, such as blue and UVB light, may be used to produce or encourage a variety of desirable biological conditions, including diminished stress and improved metabolism. A user is more likely to feel more rested, relaxed, alert, and generally in better physical and mental condition after receiving an appropriate dosage of high-energy light.

Common approaches to high-energy phototherapy involve the application of close-proximity, high-intensity UVB light to bare skin, such as is often seen using a tanning lamp or tanning bed. However, excess UVB radiation—either through direct sunlight or through a light-transmitting device—can cause mutations, breakages, and other undesirable phenomena in DNA, increasing the risk of skin cancer and, frequently, burning or otherwise damaging the patient's skin. On the other hand, general purpose lighting, such as incandescent lighting, does not deliver sufficient energy to facilitate the desired photobiomodulatory effects. Thus, for optimal therapeutic outcomes, it is necessary to manage the intensity of a UVB or blue light source, the distance from the light source to the patient, and the overall exposure or "bathing" of the patient in light of an appropriate energy.

Nonvisual stimuli may also be helpful for encouraging or producing a relaxed, recuperative state. For example, it is known that certain audio signals can reduce blood pressure, lower pulse rate, relax muscles, lower oxygen consumption, and otherwise help the body transition from a stressed or alert state into a calm, restorative state. For example, while loud, discordant audio signals can initiate a stress response whereby the brain releases cortisol and other related hormones to cope with stress-induced inflammation, soothing audio signals such as classical music, choral chanting, the sound of ocean waves, or subsonic or ultrasonic vibrations can a calming effect, relaxing the endocrine and sympathetic nervous systems and directing the body's energy toward repair and stasis. Accordingly, appropriately selected audio therapy can encourage or cause a state of relaxation in a user.

Similarly, soothing aromas such as those used in aromatherapies, are known to calm the sympathetic nervous system, relaxing the brain, downregulating the production of stress hormones such as cortisol and upregulating production of anti-inflammatory compounds such as cytokines and corticotropin-releasing hormone. A relaxation therapy may also consider other ambient factors that affect a given user, such as the user's physical comfort in the space—i.e., whether they are standing or seated on a comfortable surface, as well as whether the ambient air is sufficiently warm, cool, fresh, and clear of allergens, irritants, and the like.

Therapies such as light therapy, aromatherapy and the like may applied on multiple occasions over time as part of a therapeutic regimen. To optimize the beneficial effects of a given therapy session, or of a therapeutic regimen in toto, user information might be collected, stored, and analyzed to instruct ideal therapy settings.

Therefore, there is a need to provide devices and information-driven methods for promoting relaxation using light therapy, alone or in conjunction with other sensory therapies. Thus, it is with respect to these considerations and others that the present invention has been made.

BRIEF DESCRIPTION OF THE DRAWINGS

Non-limiting and non-exhaustive embodiments of the invention are described with reference to the following drawings. In the drawings, like reference numerals refer to like parts throughout the various figures unless otherwise specified.

For a better understanding of the present invention, reference will be made to the following Detailed Description of the Invention, which is to be read in association with the accompanying drawings, wherein.

DETAILED DESCRIPTION OF THE EMBODIMENTS

Figure 1A:
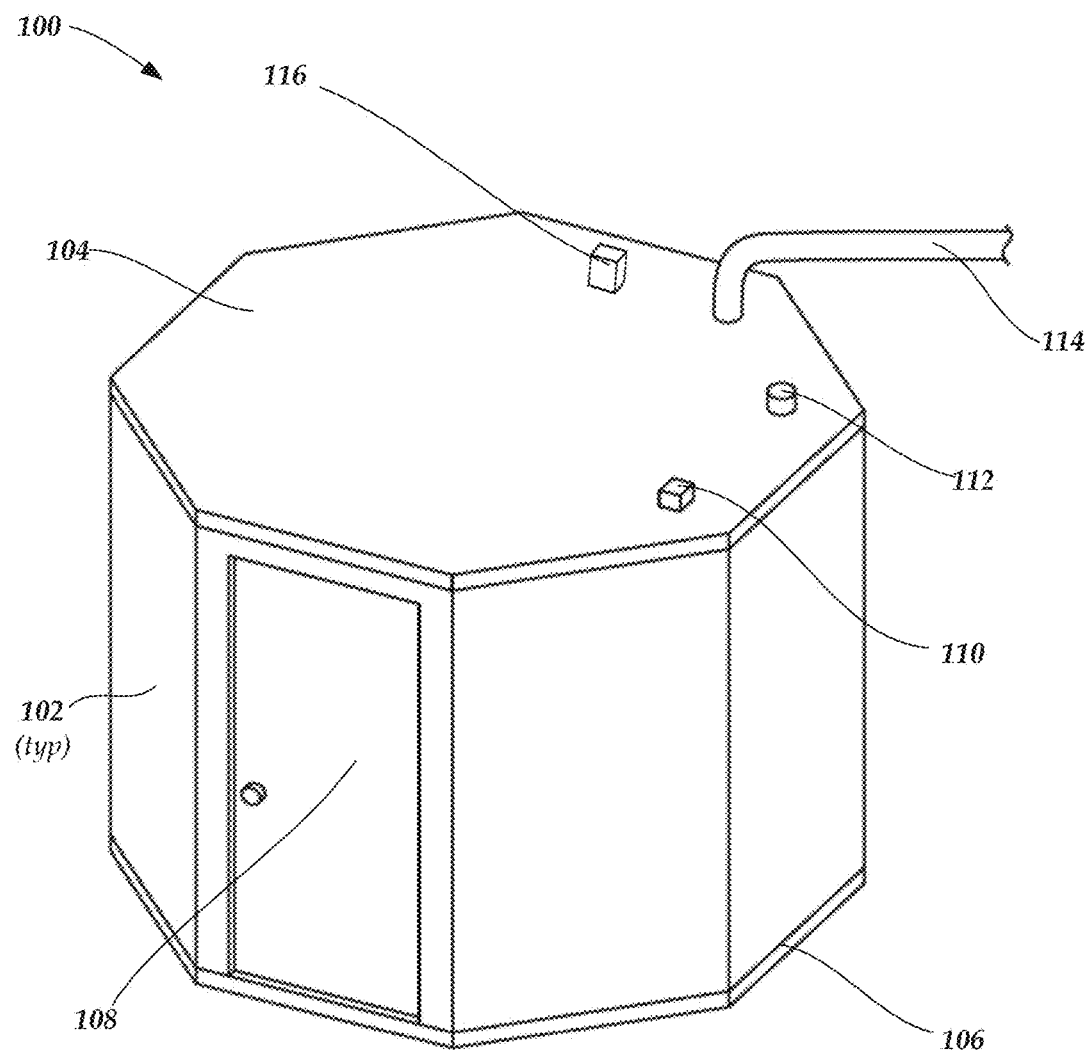
FIG. 1A illustrates a perspective view of one embodiment of an enclosure for light therapy, according to the invention.

Various embodiments are described more fully hereinafter with reference to the accompanying drawings, which form a part hereof, and which show, by way of illustration, specific embodiments. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the invention may be embodied as devices or methods. Accordingly, the various embodiments may be entirely device embodiments, entirely method embodiments, or embodiments combining device and method aspects. The following detailed description should, therefore, not be limiting.

Throughout the specification and claims, the following terms take the meanings explicitly associated herein, unless the context clearly dictates otherwise. The term "herein" refers to the specification, claims, and drawings associated with the current application. The phrase "in one embodiment" or "in at least one of the various embodiments" as used herein does not necessarily refer to the same embodiment, though it may. Furthermore, the phrase "in another embodiment" as used herein does not necessarily refer to a different embodiment, although it may. Thus, as described below, various embodiments may be readily combined.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "stress" refers to a feeling of strain and pressure, as well as associated physical indicia and underlying causal factors of stress. The term "stress" encompasses one or more physiological or mental conditions of a human being. Physiological stress conditions and indicia thereof include, but are not limited to, fatigue, malnutrition, dehydration, poor digestion, high blood pressure, above-normal heart rate, profuse sweating, heart palpitations, low body temperature (particularly when measured at body extremities such as a finger or a toe), muscle tension, headaches, elevated cortisol levels, poor sleep, elevated adrenaline levels, rapid shifts in metabolism, weight gain, premature aging, irregular breathing, weak or damaged teeth, elevated cytokine levels, cracked, frayed, thinning, or dull hair, fingernails, or toenails, and overall changes in body energy dynamics, such as transmission and absorption of light by body tissues as a measure of blood flow, blood content, and tissue activity.

Mental stress conditions and indicia thereof include, but are not limited to, feelings of anxiety, depression, discomfort, pressure, negative views of the self or others, a lack of optimism, fatigue, lethargy, irritability, guilt, feeling frayed, feeling worn out, feeling unable to cope with responsibilities or external stimuli, feeling panicked, racing thoughts, feeling disorganized, and feeling unwanted.

As used herein, the terms "relax" and "relaxation" refers to a feeling or physiological or mental condition of becoming less tense, tight, or stiff and becoming calm. Indicia of physiological relaxation, include, but are not limited to, lowered heart rate, lowered blood pressure, improved body temperature at extremities, decreased muscle tension, decreased cortisol levels, decreased cytokine levels, regular breathing, improved sleep, improved digestion, consistent metabolism, improved cellular functions such as consumption of free radical species and DNA repair, decreased adrenaline levels, taut, toned skin, full, lustrous hair, strong teeth, shiny fingernails and toenails, healthy muscle tone.

Indicia of mental relaxation include, but are not limited to, feelings of calmness, of alertness, restfulness, optimism, self-confidence, general energy, a sense of rejuvenation, improved ability to handle stress, trauma, grief, anger, and disappointment, improved mental acuity, a sense of being unhurried, and a sense of compassion for the self and for others.

As used herein, the term "light therapy" refers to the application of one or more light energies along the electromagnetic spectrum, including infrared rays, visible light, and ultraviolet rays, to a human subject for promoting or causing an improvement in one or more indicia of a disease or unhealthy condition, including physiological and mental aspects of diseases or unhealthy conditions such as stress. Light therapies of the present invention involve administering concentrated light between 290 nm and 900 nm in a non-laser form to the external tissues of a human user, such as the skin, the hair, fingernails or toenails, or the eyes of the human user, either open, through the eyelid, or through a transparent, semi-transparent, translucent, or semi-translucent lens or protective covering.

As used herein, the term "light intensity" refers to a measure of light energy emitted from a light source. Light intensity may be measured in several ways, including, for example, radiant intensity (watts per steradian), luminous intensity (lumens per steradian or candelas), and irradiance (watts per meters squared). Light intensity may be measured at or adjacent to the light source or may be measured at the point of a subject receiving the light.

As used herein, the term "light density" refers to the concentration of light waves or particles ("photons") present at a given time on a given surface or in a given three-dimensional space.

As used herein, the term "light resonance" refers to the application of light of sufficient energy to a human user to synch, encourage, or amplify resonant energy frequencies with the user's body; light resonance is believed to promote healing and well-being in human users.

The terms "bathe" or "bathing" as used herein in conjunction with a light therapy according to the invention refers to concentrating light in a three-dimensional space to surround, or partially surround, a human user. Because light travels both as a wave and as a particle, a space with a measurable presence of light waves and particles may be said to have a light density. The greater the light density in a given three-dimensional space around a human user, and the more that the light density surrounds the human user, the more the user, and any other object within the three-dimensional space, may be said to be "bathed" in the light.

As used herein, the term "aromatherapy" refers to the application of one or more pleasing aromatic compounds to a human user to promote or cause a state of relaxation or a state of decreased stress in the user. Certain naturally-occurring aromatic compounds are widely known to have a calming effect on the sympathetic nervous system via olfactory sensation, such as, for example, essences of sandalwood, vanilla, hibiscus, pine, cinnamon, lavender, chamomile, bergamot, jasmine, rose, blackberry, currant, sage, wild grass, lilac, and the like. Other scents may be more specific to encouraging relaxation in a given user, such as, for example, the smell of the user's home, a favorite food, a campfire, or a pet animal. An aromatic compound for use in an aromatherapy may come from a natural source or a synthetic source, and may be administered or delivered to the user through, for example, a burning candle, a potpourri, a perfume, a fragrance oil, a spice, or an essential oil.

As used herein, the term "audio therapy" refers to the application of one or more pleasing audio signals to a human user to promote or cause a state of relaxation or a state of decreased stress in the user. An audio therapy according to the present invention may include a sound in the subsonic, audible, or ultrasonic range. The energy of an audio therapy is sufficient to be felt, heard, or otherwise sensed by the human user, but is lower than a level that would be uncomfortable, painful, or injurious to the user. An audio therapy may take the form of, for example, classical music, nature sounds, religious chanting, modern soothing music, or ultralow soothing frequencies such as resonant frequencies or vibrations. An audio therapy may be delivered by an one or more audio therapy source such as a speaker, or, alternatively, may be delivered by a live instrument.

As used herein, the term "air therapy" refers to application of air with specific attributes to a human user and the space around the user to promote or cause a state of relaxation or a state of decreased stress in the user. Depending on the preferences of the given user, an air therapy may involve air with specified attributes such as, for example, a specified temperature or specified temperature range, a specified humidity or specified humidity range, a specified oxygen level or specified oxygen level range, air of a specified hydrostatic pressure or specified hydrostatic pressure range, a specified level of air movement (e.g., a specified level of ventilation) about the user, whether the air is treated by ionization, whether the air is treated by an ozone generator, or whether the air is filtered to remove irritants or allergens.

As used herein, the term "circadian rhythm" refers to any human biological process that displays an endogenous oscillation of about 24 hours and that is associated with a diurnal light cycle, such as, for example, bowel movements, secretion of melatonin, secretion of testosterone, blood pressure variations, sleep cycles, muscular efficiency, and metabolism.

As used herein, the term "spectrometer value" refers to an energy value measurable from the body of a human user by a spectrometer. A spectrometer is capable of measuring energy across a variety of spectra, such as, for example, electromagnetic radiation such as light waves. For example, a spectrometer may be used to measure the amount of near-infrared radiation passing through or reflecting from a given body tissue to provide a spectrometer value associated with blood flow, activity, and general condition of the tissue.

As used herein, the term "heuristic" refers techniques for learning, discovery or problem-solving by experimental, trial-and-error, and observational methods, as well as to information that is obtained through the experience of applying such techniques. By way of example, a heuristic approach to adjusting a therapeutic protocol may involve multiple iterations of performing the protocol, determining the effect of the performed protocol after each iteration and after a series of iterations, and adjusting the protocol prior to the next performance in view of the determined effects.

The following briefly describes the embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, embodiments are directed to an enclosure that provides therapy to a user, e.g., light therapy. In at least one of the various embodiments, an apparatus includes a control system for providing at least light therapy to the user. The control system includes a memory that stores instructions and a processor that executes the instructions to perform actions. For example, the actions may include generating a plurality of therapy settings based one or more of: measured user information, such as user spectrum values or user physical attributes, reported user or operator information, such as observations regarding the stress level of the user, the user's previous therapy settings, heuristic information regarding the user or a plurality of other users who have received therapy, or operator selected information; selecting one or more settings to provide therapy to a user; positioning the user within an enclosure as described below to receive therapy collecting post-therapy information regarding the user; and generating a report regarding the user based on the post-therapy information. The apparatus may also include a display that presents the report to the operator and/or the user.

As mentioned, the apparatus includes an enclosure for providing therapy to a user. In at least one of the various embodiments, the user is positioned at a particular location in the enclosure that includes a plurality of light sources located at one or more of the floor, the ceiling, or one or more walls of the enclosure. Each of the plurality of light sources is arranged to emit light towards the particular location over one or more periods of time of based on one or more selected settings for duration, intensity, ramp up, ramp down, plateau, oscillation, and the like. In at least one of the various embodiments, the light is between 290 nm and 900 nm. In at least some of the various embodiments, the light is a UV light, a blue light, or an infrared light.

The floor, the ceiling, and each wall of the enclosure is configured to focus light at the location when the light is emitted by the plurality of light sources so that the user is bathed in the light. For example, one or more lenses may be employed to focus the light emitted by one or more of the light sources at the particular location in the enclosure. In at least one of the various embodiments, the enclosure comprises a shape of an octagon. In other embodiments, the enclosure may comprise the shape of a circle, oval, sphere, square, triangle, rectangle, pentagon, hexagon, heptagon, dodecagon, or any other shape. In at least one of the various embodiments, the enclosure includes a diameter of nine feet.

In at least one of the various embodiments, the enclosure includes a resting surface for the user located within the enclosure. The resting surfaces may be a table, a bed, a chair, a stool, a cot, a hammock, or the like. The user may be positioned on the resting surface to facilitate relaxation.

In at least one of the various embodiments, the enclosure may include one or more reflective surfaces attached to one or more of the ceiling, the floor, or one or more walls for reflecting, focusing, and/or concentrating the emitted light directed to the user. In at least one of the various embodiments, the enclosure may include a container of water that is placed at a location so that the water is bathed in light emitted by the plurality of light sources during therapy. The container may be transparent, translucent, opaque, reflective, or some combination of two or more of these properties. After therapy, the user may drink the water from the container to further enhance their health.

In one embodiment, the enclosure is a fixed structure, such as a room in a building. In another embodiment, the enclosure is a portable structure that may include one of a room installed on a trailer that is towable by a vehicle, or a room within a motorized vehicle such as a motor home. In yet another embodiment, the enclosure is a temporary structure that is configured for assembly and disassembly at one or more remote locations.

The enclosure may further be configured to provide one or more of an audio therapy using an audio signal, an aromatherapy using an aroma, or an air therapy using conditioned air to the user, based on the one or more selected settings. The control system may vary one or more settings of the various therapies provided to the user within the enclosure. In at least one of the various embodiments, the control system may vary duration, intensity, and/or type of therapy, according to the selected one or more settings.

For example, the selected one or more settings may include one or more of: ramp up, ramp down, plateau, intensity up, intensity down, type of light source, type of audio source, type of aroma, amount of aroma, air temperature, air humidity, air ionization, air filtration or time period. In at least one of the various embodiments, the plurality of light sources are configured to mimic one or more diurnal light cycles over the course of a therapy session by ramping up, plateauing, and ramping down. In at least one of the various embodiments, one or more of the selected settings are operator configurable.

When the therapy is over, post-therapy protocols may be performed. In at least one of the various embodiments, the treated water may be provided to the user to drink following the light therapy. Post-therapy information regarding the user is provided and, optionally, collected by one or more of the user or the operator. The post-therapy information includes one or more of the measured and reported information regarding the user. Measured information may include, for example, measured spectrum values from the user or measured physical attributes from the user, such as, for example, blood pressure, heart rate, and body temperature as measured at a body extremity, such as fingers and toes. When a human body is relaxed, the extremities such as fingers are warmer because the blood vessels are relaxed. When a human body is stressed, blood vessels constrict and fingers tend to cool off.

In one or more of the various embodiments, reported information regarding the user may include, for example, the user's reported stress level, physical sensations, feelings of well-being, and the like. A report regarding the user is generated based on the post-therapy information to analyze the effect of the therapy and to inform a future course of action. The report may be displayed on a user interface that includes one or more of: an analysis of the current therapy provided to the user; an analysis of previous therapy provided to the user; a comparative analysis of therapy provided to the user and other users that previously received therapy, or the like.

In yet another of the various embodiments, a global positioning system (GPS), transceiver is employed to detect a physical location of the enclosure. The enclosure's location is employed by the control system to localize the written language and the units of measure that are used to display one or more of the measured information, reported information, historical information, operator selected information, plurality of settings, selected settings, or the report. For example, if the GPS sensor detected that the enclosure was located in Mexico, the control system would localize the language to Spanish and the units of measure would be metric, i.e., kilograms and meters instead of pounds and feet.

The invention further includes a computer readable non-transitory storage media that includes instructions for providing therapy to a user positioned within an enclosure according to the invention.

FIG. 1A illustrates one embodiment of an apparatus according to the invention. As shown in the figure, the apparatus includes enclosure 100 with ceiling 104, floor 106, and walls 102 extending substantially vertically between ceiling 104 and floor 106. Each of walls 102 is sufficiently sized so that human users of varying height may comfortably enter and stand or rest at a location in enclosure 100. Entry and exit relative to enclosure 100 may be facilitated by a portal such as, for example, door 108. In one embodiment, enclosure 100, is a fixed structure such as a room inside a building. In another embodiment, the enclosure is a portable structure, such as, for example, a room in a mobile home or a room on a vehicle trailer. In another embodiment, the enclosure is a temporary structure that is configured for assembly and disassembly in one or more remote locations. In another embodiment, the enclosure may be manufactured and sold in, for example, the form of a kit for assembly at a remote location.

As shown in the figure, in at least one of the various embodiments, enclosure 100 is arranged in the shape of an octagon. When viewed from directly above or directly below, each of ceiling 104 and floor 106 defines a plane having eight equivalent angles and eight equivalent sides, each of the eight sides corresponding to walls 102. As will be explained further with reference to FIGS. 1C and 2C, enclosures of certain shapes are more suited to provide light therapy to a user than other shapes. Thus, the shape of enclosure 100 may be selected according to certain criteria described herein. In other various embodiments, an enclosure may assume the shape of, for example, a circle, an oval, a sphere, a square, a triangle, a rectangle, a pentagon, a hexagon, a heptagon, an octagon, a nonagon, a dodecagon, and the like.

Figure 1B:
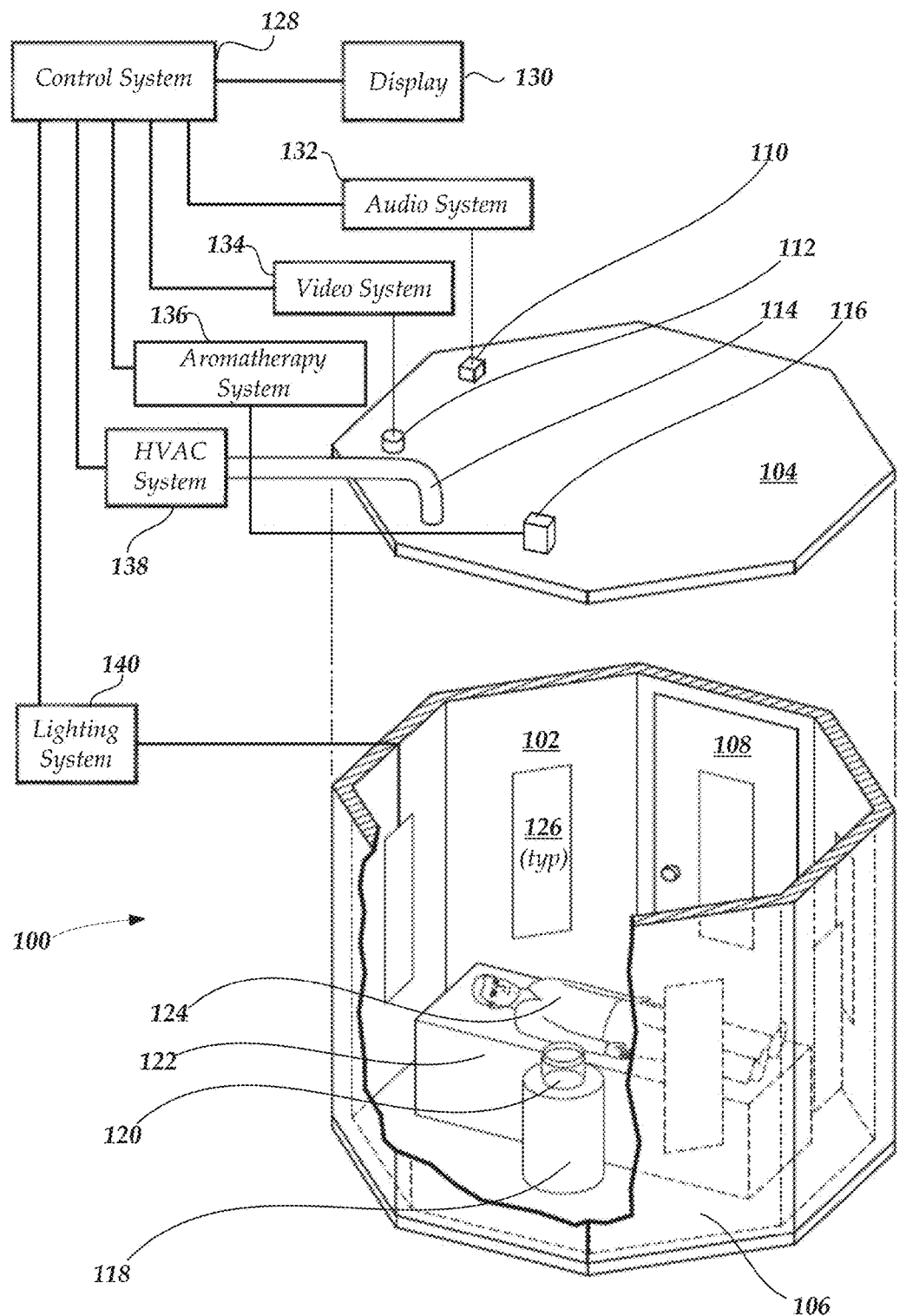
FIG. 1B illustrates an exploded and cut-away view of the enclosure of FIG. 1A with a control system and with a user at rest therein.

As will be better understood with reference to FIG. 1B, at least one of the various embodiments includes control system 128 which may include a memory and a processor (not shown) and/or logic circuitry such as an Application Specific Integrated Circuit (ASIC), and the like. Control system 128, may be configured to, for example, receive, store, and execute instructions that are subsequently executed to perform actions such as providing, monitoring, analyzing, and reporting on therapy provided to user 124.

As will described in further detail with reference to FIGS. 4A-4E, the actions may include, for example: generating a plurality of settings for the therapy; selecting one or more of the plurality of settings to provide therapy to user 124; positioning user 124 at a location within enclosure 100, wherein enclosure 100 includes plurality of light sources 126 and wherein enclosure 100 is configured to direct light at the location; providing light therapy to user 124 with light emitted by plurality of light sources 126, over one or more periods of time, directed to the location based on the selected one or more settings; monitoring the therapy provided to user 124; providing post-therapy information regarding user 124; and generating a report regarding therapy provided to user 124 based on the post-therapy information. The report may include analysis of the therapy provided to user 124. In at least one of the various embodiments, display 130 is coupled to control system 128. Display 130 presents the report to one or more of an operator of control system 128 (not shown) and user 124.

In FIG. 1B, enclosure 100 is rotated 180° with respect to the view provided in FIG. 1A and is depicted with greater detail in an exploded and cut-away view. As shown in the figure, enclosure 100 includes plurality of light sources 126 located about enclosure 100 along each of walls 102. It will be appreciated that plurality of light sources 126 may additionally, or alternatively, be located along one or more of floor 106 or ceiling 104. One or more of plurality of light sources 126 may be configured to deliver light of one or more wavelengths, such as 290 nm to 900 nm. In one of the various embodiments, one or more of plurality of light sources 126 may be controlled by lighting system 140, which may provide various functions, e.g., dimming, ramping up, ramping down, hold, oscillation, pulse(s), and off. The light delivered by plurality of light sources 126 may be, one or more of an ultraviolet light, such as a fluorescent UVB light or an incandescent UVA light, a light in the visible spectrum, such as a blue light, or infrared light, such as a heat light. Additionally, one or more of plurality of light sources 126 may include one or more lenses (not shown) to further direct and focus or defocus emitted light towards a location within enclosure 100.

In at least some of the various embodiments, one or more of ceiling 104, floor 106, or walls 102 are configured to focus the light at the location, which may be in the center of enclosure 100 or may be at a different location. For example, each walls 108 may be at an even distance from the location. Alternatively or in addition, one or more of ceiling 104 or walls 108 may be convex, concave, domed, or vaulted.

In at least some of the various embodiments, enclosure 100 may further include a reflective surface attached to one or more of ceiling 104, floor 106, or walls 102. For example, the interior of enclosure 100 may include Mylar™ attached along all or a portion of walls 102, ceiling 104 and floor 106. Alternatively, floor 106 may be constructed, in whole or in part, of stainless steel, or may have a coating of a reflective substance, such as paint.

As shown in the figure, enclosure 100 includes resting surface 122 located within enclosure 100 for user 124 to rest comfortably while receiving therapy. As shown in FIG. 1B, the resting surface 122 is a bed. In various embodiments, the resting surface may alternatively be a table, a chair, a couch, a reclining chair, a stool, a cot, a hammock, or the like.

In at least one of the various embodiments, resting surface 122 is composed of a reflective material or, alternatively, is composed of a translucent, transparent, or semi-transparent material to further permit light emitted by plurality of light sources 126 to further reflect the emitted light onto user 124. Resting surface 122 is arranged at a suitable height so that a user 124 resting thereon may be bathed in light from the plurality of light sources 126, as shown for example, in FIGS. 1C and 2C. Accordingly, resting surface 122 may be adjustable to place user 124 in an optimal position for receiving light from plurality of light sources 126.

Figure 4A:
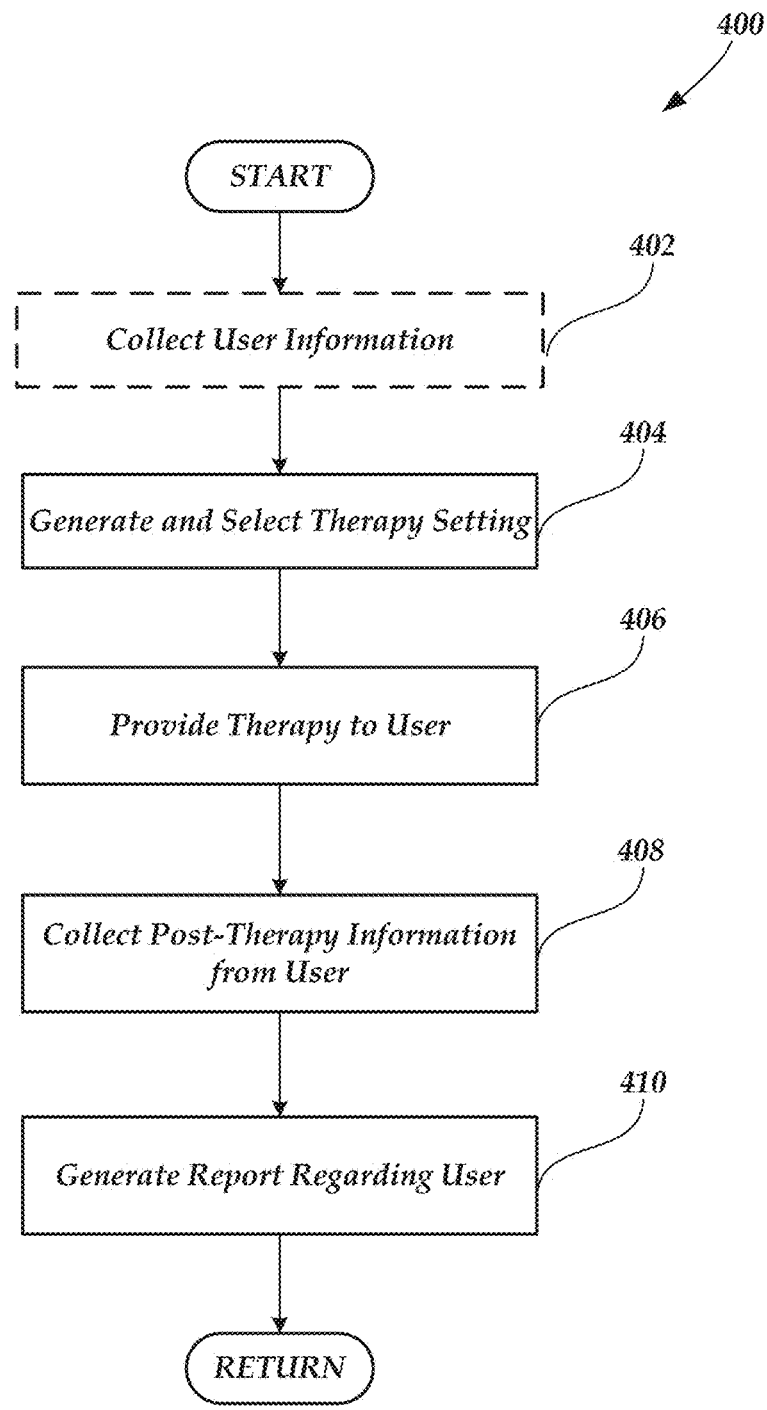
FIG. 4A illustrates a logical flow diagram generally showing one embodiment of a method for providing therapy to a user generating a report regarding the user based on user post-therapy information, according to the invention.
Figure 4B:
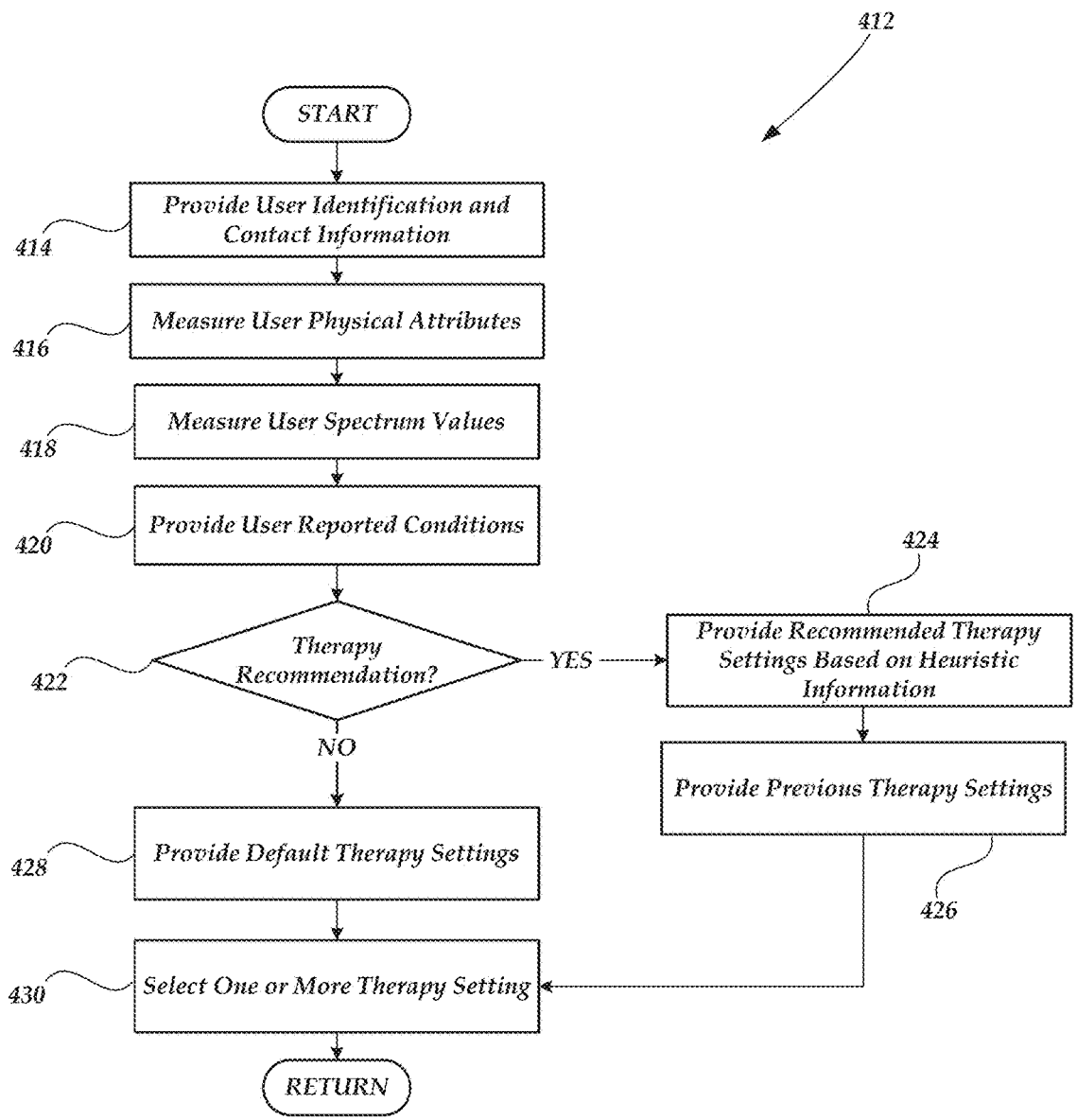
FIG. 4B illustrates a logical flow diagram generally showing one embodiment of a method for providing user information and selecting therapy values for the user before a providing therapy to the user, according to the invention.

As will be described in further detail with respect to FIG. 4D, the enclosure 100 may further include water to be treated by the light therapy and subsequently provided to user 124 to drink after the therapy has been provided to user 124. Treatment of the water by the light emitted by plurality of light sources 126 may sterilize, purify, energize, or in other ways reinvigorate the water. In the embodiment shown in FIG. 1B, the water is stored in container 120. Container 120 rests on table 118 at a location adjacent to resting surface 122 within enclosure 100.

An apparatus according to the invention may further provide one or more additional therapies to user 124, including, for example, an aromatherapy, an audio therapy, or an air therapy. Accordingly, as shown in FIG. 1B, enclosure 100 further includes one or more audio therapy source 110 coupled to audio system 132, one or more aromatherapy source 116 coupled to aromatherapy system 136, and one or more of heating, ventilation, air conditioning (HVAC) device 114 coupled to HVAC system 138. Also, in one or more of the various embodiments, HVAC system 138 can provide extra oxygen for user 124 inside enclosure 100. Plurality of light sources 126 is likewise coupled to lighting system 140, which may provide various functions to control plurality of light sources 126, e.g., dimming, ramping up, ramping down, hold, oscillation, pulse(s), and off. Enclosure 100 further includes one or more video cameras 112 coupled to video system 134 for monitoring the safety of user 124 when the user is inside enclosure 100. Each of audio system 132, video system 134, aromatherapy system 136, HVAC system 138, and lighting system 140 is coupled to and controlled by control system 128. Display 130 is coupled to control system 128, which enables an operator (not pictured) to, among other things, control one or more of the various types of therapies and their corresponding settings.

For example, the operator may use control system 128 to control the wavelength, intensity, duration, ramp up, ramp down, dimming, and delivery cycle of light emitted by the plurality of light sources 126 to the user 124. In at least some of the various embodiments, the period of time that one or more therapies are provided may be relatively short (a few minutes), or a magnitude longer, depending on, for example, the settings configured by the operator for user 124. For example, depending on the intensity of the light, a therapy session of approximately 3 minutes may generate between 5,000 and 7,000 International Units (IUs) of Vitamin D in user 124, while a therapy session of approximately 18 minutes may generate about 40,000 IUs in user 124.

In at least one of the various embodiments, the light provided to user 124 in a light therapy session may be set to mimic one or more diurnal cycles, e.g., one or more cycles of: a "sunrise" phase followed by a "daylight" phase and then a "sunset" phase, over the course of the therapy session. Mimicry of one or more diurnal cycles may serve to reset or stimulate the natural circadian rhythms of user 124, thereby promoting, for example, improved healing, sleep, digestion, energy, serotonin production, overall mood, or awareness. For example, a light therapy session may be characterized by a "sunrise" phase, wherein the intensity of the light ramps up, followed by a peak intensity, and then followed a "sunset" phase, wherein the intensity of the light decreases.

It will be appreciated that in at least some of the various embodiments, the intensity or type (e.g., wavelength, polarized, non-polarized, filtered or non-filtered) of light from the plurality of light sources 126 may be varied in phases over the course of a therapy session. Accordingly, the light may be ramped up slowly or quickly, plateau for a short period of time or a long period of time, ramped down slowly or quickly, or vary in intensity, type, or source. For example, in one setting, the light intensity may be set to, ramp up slowly, ramp down quickly, ramp up again quickly, and then ramp down slowly over the course of a therapy session. A ramping up or ramping down of the light may occur gradually or stepwise; a step during a ramping up or a ramping down phase may be of the same length or a different length from another step during the same ramping up or ramping down phase.

Thus, in one setting, the light may ramp up quickly, plateau for the majority of the therapy session, and then ramp down quickly. In another setting, the light may oscillate, continuously ramping up, peaking, and ramping down several times over the course of a therapy session. In yet another setting, the light may ramp slowly for the majority of the therapy session, peak briefly, and then ramp down quickly. In yet another setting, the light may ramp generally up over the course of a therapy session but experience small ramp down periods or dips as it ramps generally up.

In yet another setting, the type of light provided may vary between a visible light such as a blue light, a UVB light, and an infrared light over the course of the therapy session. In still another setting, the light may dim completely and no light may be provided for one or more intervals during the light therapy session. In still another setting, the type of light provided may be continuous over the course of the therapy session and may include one or more of a visible light, a UVB light, or an infrared light. A light setting may be configurable by the operator during the course of a therapy session based on, for example, feedback from the user. However, the invention is not so limited, and it will be appreciated that many other light therapy settings of many different variations may be selected to provide light therapy to a user 124.

In at least one of the various embodiments, control system 128 is configured to enable the operator (not shown) to control, for example, the delivery, selection, volume, sound qualities, duration, and arrangement of one or more relaxing audio signals delivered by an one or more audio therapy source 110 to user 124 inside enclosure 100. One or more audio therapy sources 110 may deliver, for example, classical music, such as works by composers such as Chopin, Bach, Mozart, Handel, Beethoven, Haydn, and the like, which is believed to have a soothing effect on the sympathetic nervous system and to have a regenerative effect at the cellular level. Additionally or alternatively, one or more audio therapy sources 110 may deliver other forms of soothing music or one or more nature sounds, such as, for example, the sound of ocean waves, or of wind leaves on a tree, or of a running river, or of birds singing. In another example, the one or more audio therapy source may deliver Buddhist or Gregorian chanting. In various embodiments, audio therapy sources 110 may emit one or more audio signals outside the range of human hearing, such as in a sonic, a subsonic, or an ultrasonic range.

In at least one of the various embodiments, the ultrasound audio signal may take the form of a wave having any pitch and any frequency, though lower pitches or frequencies may be preferred to promote relaxation, while higher pitches frequencies may be preferred to promote certain forms of healing. In one setting, the ultrasound wave is set to mimic a healthy resting heart rate of the user to induce or promote a relaxed, regular heartbeat in the user. In another setting, the ultrasound wave may be higher, such as, for example, between 800,000 Hz and 2,000,000 Hz, to stimulate blood flow and healing in one or more tissues of user 124.

In at least one of the various embodiments, the one or more audio signals provided to user 124 is synched to one or more settings of lighting system 140. For example, the one or more audio signals may crescendo as the light ramps up, e.g., during a "sunrise" phase, and may diminish in volume or intensity as the light ramps down, e.g., during a "sunset" phase. In addition, audio system 132 may be used by the operator to communicate with user 124 inside enclosure 100. For example, one or more audio therapy sources 110 may provide an auditory notification, such as, for example, a notification tone, a spoken message, or a shift in music, to user 124 indicating that the light therapy is complete or is nearing completion.

The intensity or type of the one or more audio signals provided by one or more audio therapy sources 110 may be varied in phases over the course of a therapy session. Accordingly, the one or more audio signal may be ramped up slowly or quickly, plateau for a short period of time or a long period of time, ramped down slowly or quickly, or vary in intensity, type, or source. For example, in one setting, the one or more audio signal may be set to ramp up slowly, ramp down quickly, ramp up again quickly, and then ramp down slowly over the course of a therapy session. A ramping up or ramping down of the one or more audio signal may occur gradually or stepwise; a step during a ramping up or a ramping down phase may be of the same length or a different length from another step during the same ramping up or ramping down phase.

Thus, in one setting, the one or more audio signal may ramp up quickly, plateau for the majority of the therapy session, and then ramp down quickly. In another setting, the one or more audio signal may oscillate, continuously ramping up, peaking, and ramping down several times over the course of a therapy session. In yet another setting, the one or more audio signal may ramp slowly for the majority of the therapy session, peak briefly, and then ramp down quickly. In yet another setting, the one or more audio signal may ramp generally up over the course of a therapy session but experience small ramp down periods or dips as it ramps generally up.

In yet another setting, the type of the one or more audio signal provided may vary between an audible sound, a subsonic sound, and an ultrasonic sound, or any combination thereof, over the course of the therapy session. In still another setting, the one or more audio signal may dim completely and no audio signal may be provided for one or more intervals during the therapy session. In still another setting, the type of the one or more audio signal provided may be continuous over the course of the therapy session and may include one or more of an audible sound, a subsonic sound, or an ultrasonic sound. An audio setting may be configurable by the operator during the course of a therapy session based on, for example, feedback from the user. However, the invention is not so limited, and it will be appreciated that many other audio therapy settings of many different variations may be selected to provide audio therapy to user 124.

In at least one of the various embodiments, the control system 128 is configured to enable an operator to control the provision, type, and amount of one or more aromas provided by one or more aromatherapy sources 116 to user 124 in enclosure 100. In at least some of the various embodiments, the provided one or more aromas are generally known to promote relaxation. Such aromas may include, for example, sandalwood, vanilla, hibiscus, pine, cinnamon, lavender, chamomile, bergamot, jasmine, rose, lilac, blackberry, currant, sage, lemon grass, and the like, separately or in any combination or sequence. Additionally or alternatively, a specific one or more aroma that is known to be relaxing to a particular user may be provided. The one or more aromas provided to user 124 may vary in concentration over the course of a therapy session. The one or more aromatherapy setting is regulated by aromatherapy system 136, which may sample air within enclosure 100 and adjust the amount or type of aroma provided in accordance with predetermined settings or feedback from user 124. In addition or alternatively, the one or more aromatherapy therapies are selectable and configurable by the operator.

In at least one of the various embodiments, the aroma therapy provided to user 124 is synched to one or more settings of lighting system 140. For example, the amount of aroma may increase in intensity as the light ramps up, e.g., during a "sunrise" phase, and may decrease in intensity as the light ramps down, e.g., during a "sunset" phase. The intensity or type of aroma provided by one or more aromatherapy sources 116 may be varied in phases over the course of a therapy session. Accordingly, the amount of aroma may be ramped up slowly or quickly, plateau for a short period of time or a long period of time, ramped down slowly or quickly, or vary in intensity, type, or source. For example, in one setting, the amount of aroma may be set to, ramp up slowly, ramp down quickly, ramp up again quickly, and then ramp down slowly over the course of a therapy session. A ramping up or ramping down of the amount of aroma may occur gradually or stepwise; a step during a ramping up or a ramping down phase may be of the same length or a different length from another step during the same ramping up or ramping down phase.

Thus, in one setting, the amount of aroma may ramp up quickly, plateau for the majority of the therapy session, and then ramp down quickly. In another setting, the amount of aroma may oscillate, continuously ramping up, peaking, and ramping down several times over the course of a therapy session. In yet another setting, the amount of aroma may ramp slowly for the majority of the therapy session, peak briefly, and then ramp down quickly. In yet another setting, the amount of aroma may ramp generally up over the course of a therapy session but experience small ramp down periods or dips as it ramps generally up.

In yet another setting, the type of the one or more aromas provided to user 124 may vary over the course of the therapy session. In still another setting, the amount of the one or more aromas may decrease completely, and no aroma may be provided for one or more time intervals during the aroma therapy session. In still another setting, the type of the one or more aromas provided may be continuous over the course of the therapy session and may include one or more different aromas. However, it will be appreciated that many other aromatherapy settings of many different variations may be selected to provide aroma therapy to user 124.

In at least one of the various embodiments, air therapy is provided to the user using one or more HVAC device 114. Accordingly, one or more of the temperature, humidity, and air movement within enclosure 100 may be regulated to meet the preferences of a given user 124 or to meet predetermined settings. The air therapy may further include configuring the one or more HVAC device 114 to filter the air to, for example, remove allergens such as pollen, ragweed, dust, and the like, or to ionize and sterilize the air in enclosure 100. The air therapy may also include providing extra oxygen inside the enclosure of user 124.

In at least one of the various embodiments, one or more of temperature, humidity, oxygen, and/or air flow provided to user 124 is synched to one or more settings of the lighting system 140. For example, one or more of the temperature, oxygen, humidity, and air movement may increase as the light ramps up, e.g., during a "sunrise" phase, and may diminish in volume or intensity as the light ramps down, e.g., during a "sunset" phase. In one example, the air movement may increase from stillness to a gentle breeze during a "sunrise" phase.

One or more settings for providing air therapy may vary over the course of a therapy session. Accordingly, one or more of the temperature, humidity, oxygen, or air movement may be ramped up slowly or quickly, plateau for a short period of time or a long period of time, ramped down slowly or quickly, or vary in intensity, type, or source. For example, in one setting, one or more of the temperature, humidity, oxygen, and/or air movement may be set to ramp up slowly, ramp down quickly, ramp up again quickly, and then ramp down slowly over the course of a therapy session. A ramping up or ramping down of one or more of temperature, oxygen, humidity, and/or air movement may occur gradually or stepwise; a step during a ramping up or a ramping down phase may be of the same length or a different length from another step during the same ramping up or ramping down phase.

Thus, in one setting, one or more of the temperature, oxygen, humidity, and/or air movement may ramp up quickly, plateau for the majority of the therapy session, and then ramp down quickly. In another setting, one or more of the temperature, oxygen, humidity, and/or air movement may oscillate, continuously ramping up, peaking, and ramping down several times over the course of a therapy session. In yet another setting, one or more of the temperature, humidity, or air movement may ramp slowly for the majority of the therapy session, peak briefly, and then ramp down quickly. In yet another setting, one or more of the temperature, humidity, or air movement may ramp generally up over the course of a therapy session but experience small ramp down periods or dips as it ramps generally up.

In at least one of the various embodiments, one or more air therapy settings may be configurable by the operator during the course of a therapy session based on, for example, feedback from user 124. However, it will be appreciated that many other air therapy settings of many different variations may be selected to provide air therapy to user 124.

Figure 1C:
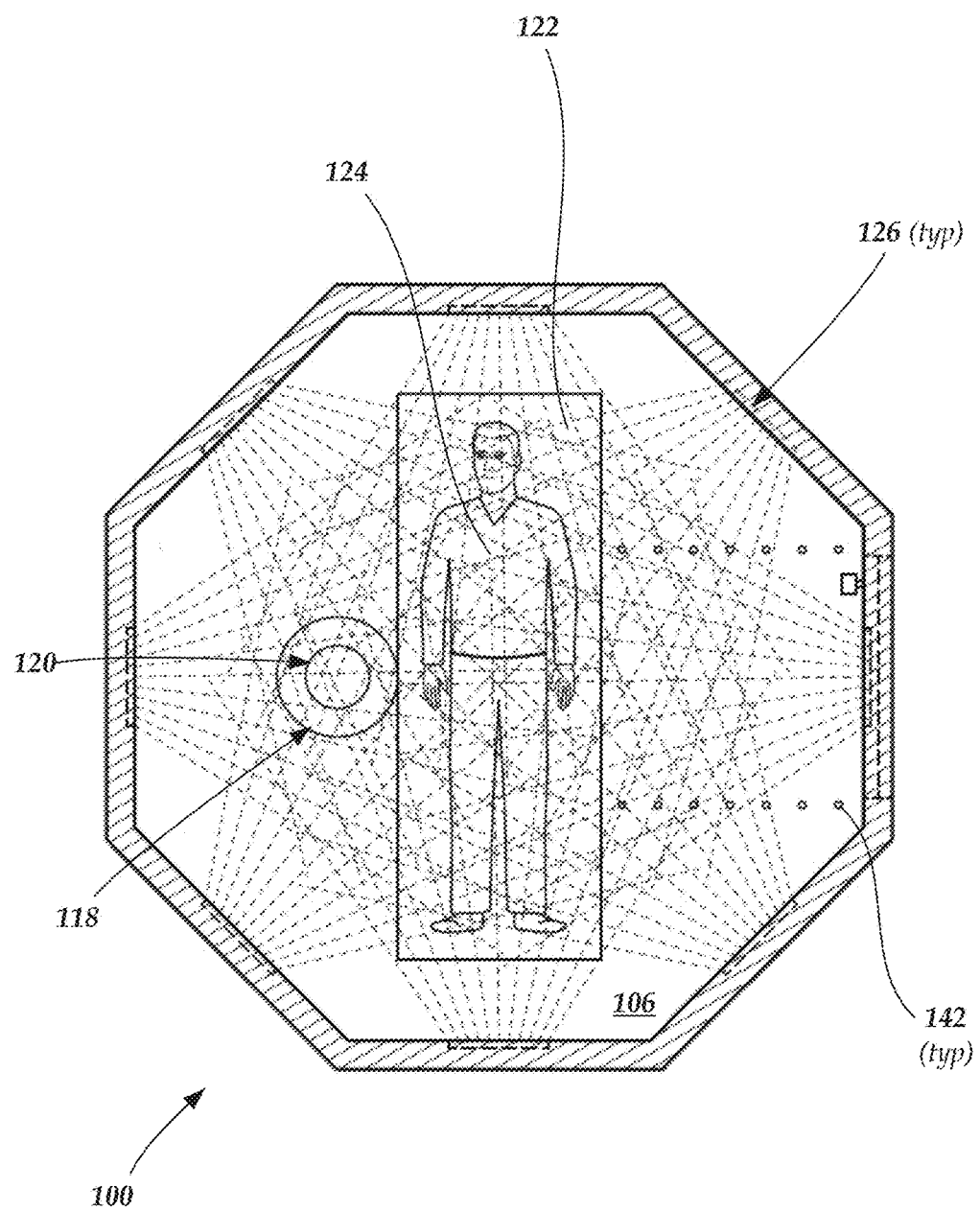
FIG. 1C illustrates a cut-away top plan view of the enclosure of FIG. 1A with a user receiving a light therapy therein, according to the invention.

FIG. 1C shows a top plan view of the enclosure 100 of FIG. 1B with ceiling 104 removed. The enclosure 100 and plurality of light sources 126 are configured and arranged to bathe user 124 in light when the user is at a location inside enclosure 100. As shown in the figure, enclosure 100 is arranged in the shape of an octagon. An octagonal enclosure, such as enclosure 100, provides a desirably high number of directions from which light may be directed toward user 124 while also maximizing the area in which light from the plurality of light sources 126 overlaps. In one embodiment, enclosure 100 includes a diameter of nine feet. In various other embodiments, enclosure 100 includes a diameter of substantially less than nine feet or substantially more than nine feet. The length of a diameter of the enclosure 100 must be long enough for user 124 to rest inside and position themselves at a center location within enclosure 100 to optimize the beneficial effects of light therapy.

In at least one of the various embodiments, the enclosure 100 assumes a four sided shape such as a square, or an equilateral, that is, each side is of the same length and each two adjacent sides form an angle of the same degree. As a result, in such embodiments, each of the plurality of light sources 126 is located an equal distance from the location of the user 124 when the user 124 is located in the center of enclosure 100. However, it will be understood that a location of user 124 need not be in a center of enclosure 100; wherever the location is within enclosure 100, floor 106, the ceiling 104 and each wall 102 of the enclosure, as well as plurality of light sources 126 disposed therein, are configured to focus light at the location.

In at least one of the various embodiments, each of the plurality of light sources 126 is located within one or more walls 102. Accordingly, light (dashed lines) from plurality of light sources 126 is focused toward the location of the user 124 within the enclosure 100. As shown in the figure, user 124 is laying/resting on resting surface 122 at a location near a center of enclosure 100, and container 120 of water is at rest on table 118 adjacent to resting surface 122. Light from the plurality of light sources 126 is directed to form a three-dimensional region or "bubble" of maximum light density around the location of the user 124, which bathes user 124 and, optionally, container 120 of water in the emitted light. In some instances, resonance of the emitted light waves may be achieved to further promote the intensity of the light therapy provided to user 124.

In at least one of the various embodiments, one or more LED lights 142 may be located along at least a portion of floor 106, ceiling 104, and/or one or more walls 102. One or more LED lights 142 may help orient user 124 and assist the user in safely entering and exiting enclosure 100 when plurality of light sources 126 are not providing visible light, such as prior to or following a therapy session, or when the light provided is light that is not within a visible light spectrum.

Figure 2A:
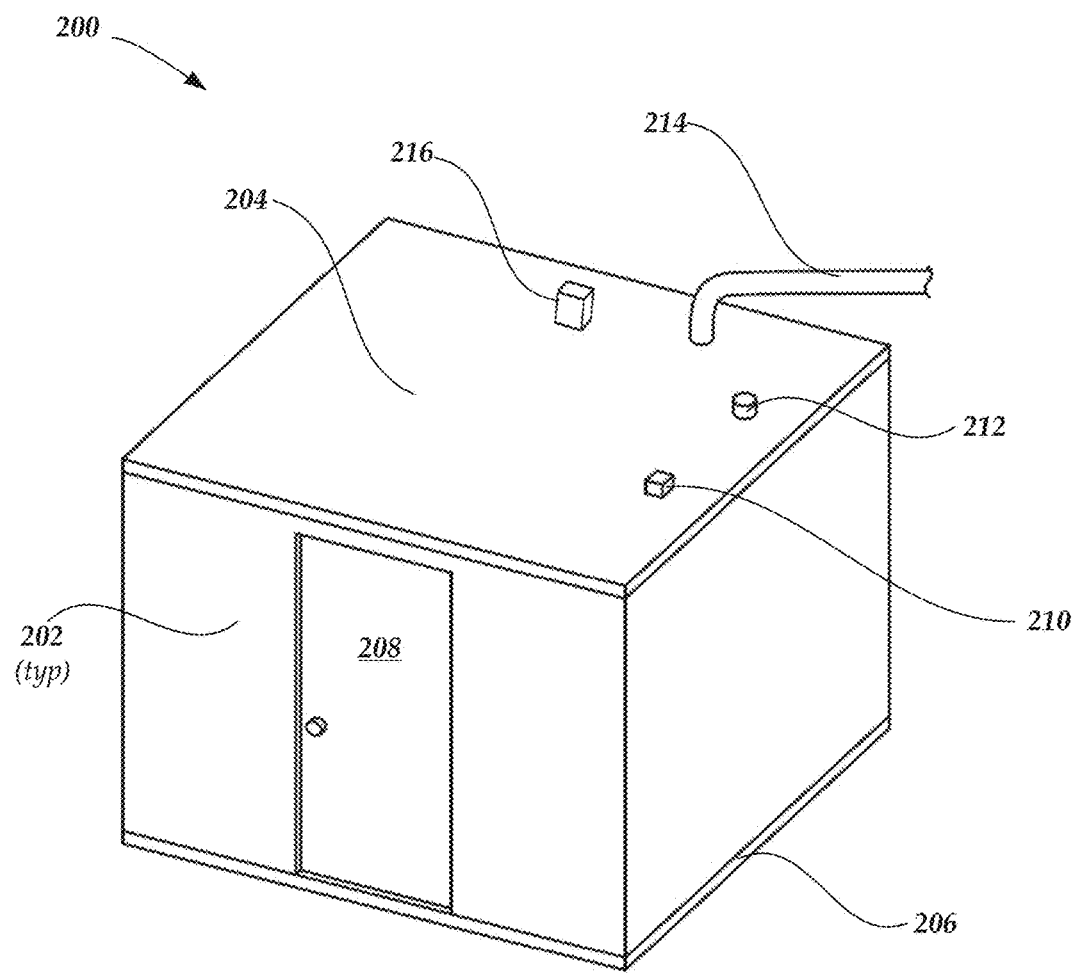
FIG. 2A illustrates a perspective view of another embodiment of an enclosure for light therapy, according to the invention.
Figure 2B:
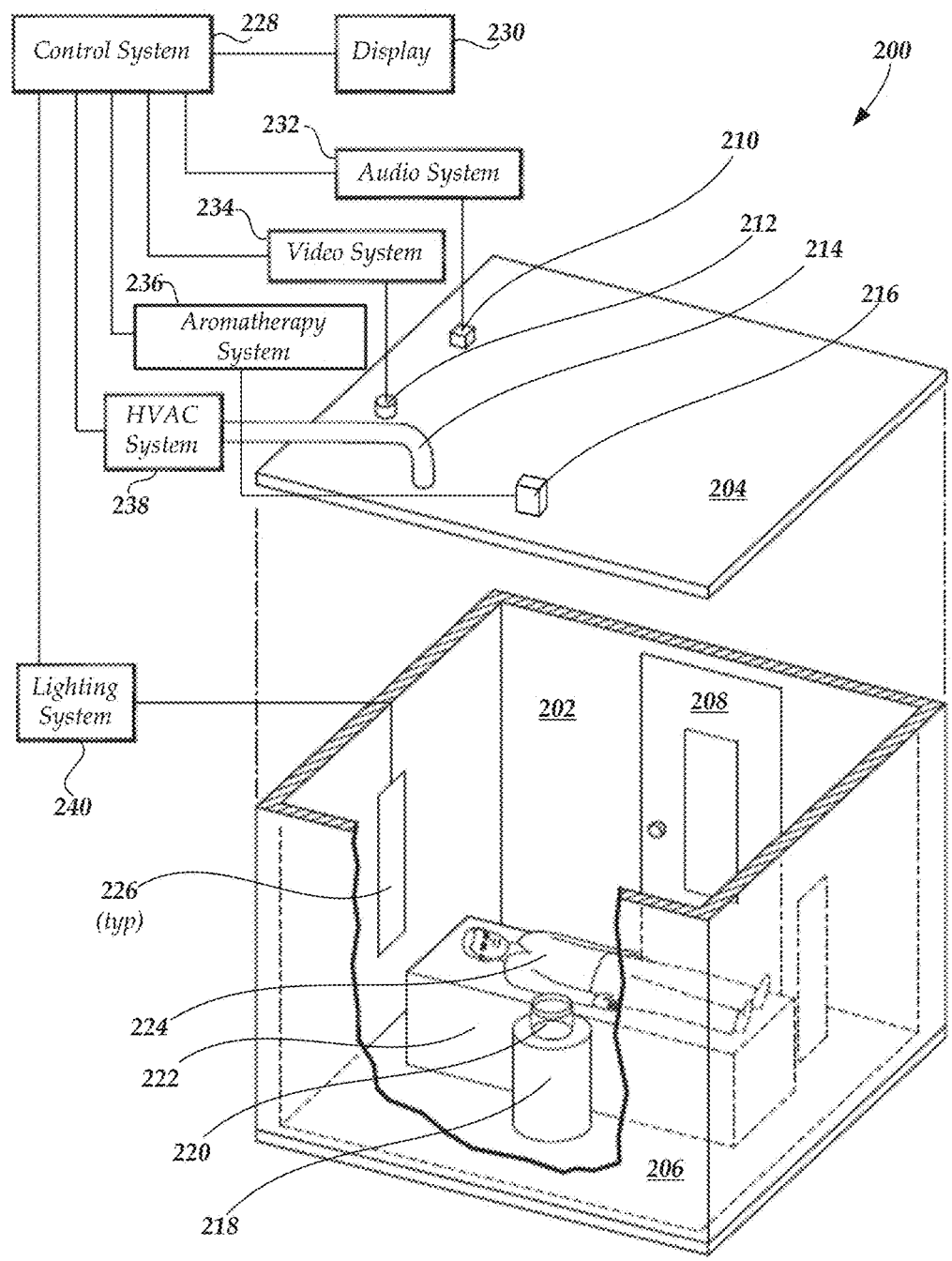
FIG. 2B illustrates an exploded and cut-away view of the enclosure of FIG. 2A with a control system and with a user at rest therein.
Figure 2C:
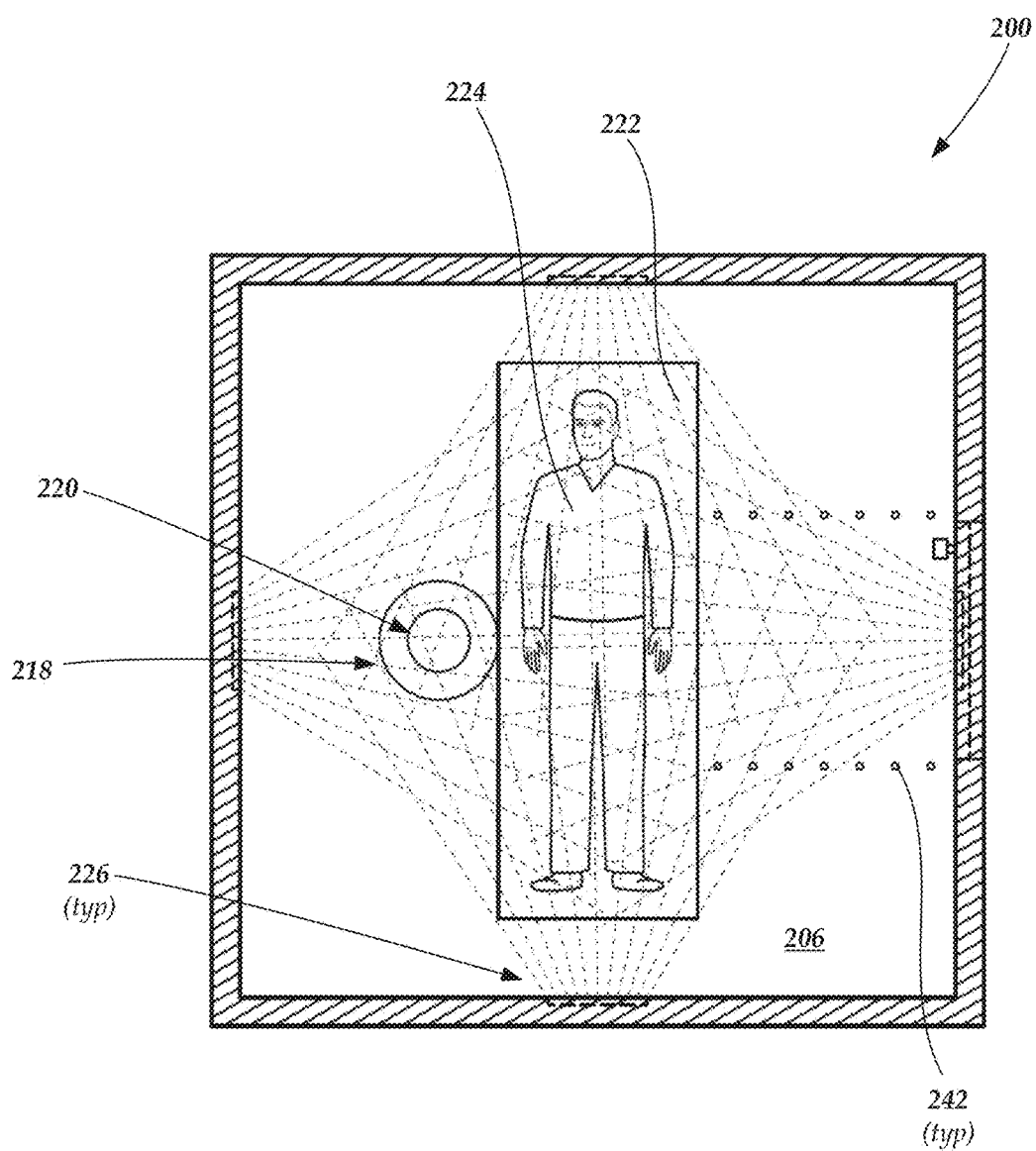
FIG. 2C illustrates a cut-away top plan view of the enclosure of FIG. 2A with a user receiving a light therapy therein, according to the invention.

FIGS. 2A-2C depict another embodiment of an apparatus. As shown in FIG. 2A, the apparatus includes enclosure 200 with ceiling 204, floor 206, and walls 202 that are configured in a square shape. As shown in FIG. 2B, the enclosure 200 includes a plurality of light sources 226 located along and within each of walls 202, as well as one or more audio therapy source 210 coupled to an audio system 232, one or more aromatherapy source 216 coupled to an aromatherapy system 236, and one or more heating, ventilation, and air conditioning (HVAC) device 214 coupled to an HVAC system 238. The plurality of light sources 226 is likewise coupled to a lighting system 240. Enclosure 200 further includes one or more video camera 212 coupled to a video system 234 for monitoring the safety of the user 224 when the user 224 is in the enclosure 200. Each of the audio system 232, the video system 234, the aromatherapy system 236, the HVAC system 238, and the lighting system 240 is coupled to and controlled by the control system 228, which is in turn coupled to display 230 to permit an operator (not pictured) to, among other things, control therapy settings.

It will be understood that in the present embodiment, one or more setting of one or more of: a light therapy provided by the plurality of light sources 226; an audio therapy provided by the one or more audio therapy source 210; an aromatherapy provided by the one or more aromatherapy source 212; or an air therapy provided by the one or more HVAC device 214 may be controlled and varied, respectively, in the same fashion as the light therapy from the plurality of light sources 126, an audio therapy provided by the one or more audio therapy source 110, an aromatherapy provided by the one or more aromatherapy source 112, or an air therapy provided by the one or more HVAC device 114, described previously with respect to the embodiment shown in FIGS. 1A-1C. Accordingly, for example, the light provided to the user 224 in a therapy session may be set to mimic one or more diurnal cycles, e.g., one or more cycles of: a "sunrise" phase followed by a "daylight" phase and then a "sunset" phase, over the course of the therapy session.

Within the enclosure 200 of the present embodiment, the plurality of light sources 226 is located along and within each of walls 202. A resting surface 222 for user 224 is located at a location along the center of floor 206. Container 220 containing water rests on table 218 adjacent to resting surface 222. It will be understood that while the location of resting surface 222, the user 224, and container 220 may be shown in the center of enclosure 200, the location may also be in another area of enclosure 200. Floor 206, ceiling 204, and each wall 202 of enclosure 200, as well as the plurality of light sources 226 is configured to focus the emitted light at the location to enhance light therapy provided to user 224.

An example of providing light therapy using enclosure 200 is illustrated in FIG. 2C, wherein light from plurality of light sources 226 is focused to form a three-dimensional region or "bubble" of maximum light density around the location, bathing user 224 in light, and, optionally, container 220 in the emitted light. In some instances, resonance of the emitted light may be achieved to further promote the effectiveness of light therapy provided to user 224. One or more LED lights 242 may be located along at least a portion of one or more of floor 206, ceiling 204, and walls 202. One or more LED lights 241 orient user 224 and assist the user in safely entering and exiting enclosure 200 when plurality of light sources 226 is not providing visible light, such as prior to or following a light therapy session, or when the emitted light is provided in a non-visible spectrum. Additionally, one or more of plurality of light sources 226 may include one or more lenses (not shown) to further direct and focus or defocus emitted light towards a location within enclosure 200.

It will be understood by reference to FIGS. 1C and 2C that enclosures 100, 200 having different configurations, including the location and number of the plurality of light sources 126, 226, may provide more or less light therapy to a user 124, 224 based on the size, shape, and light density of the "bubble" of light that bathes the user 124, 224.

Figure 3:
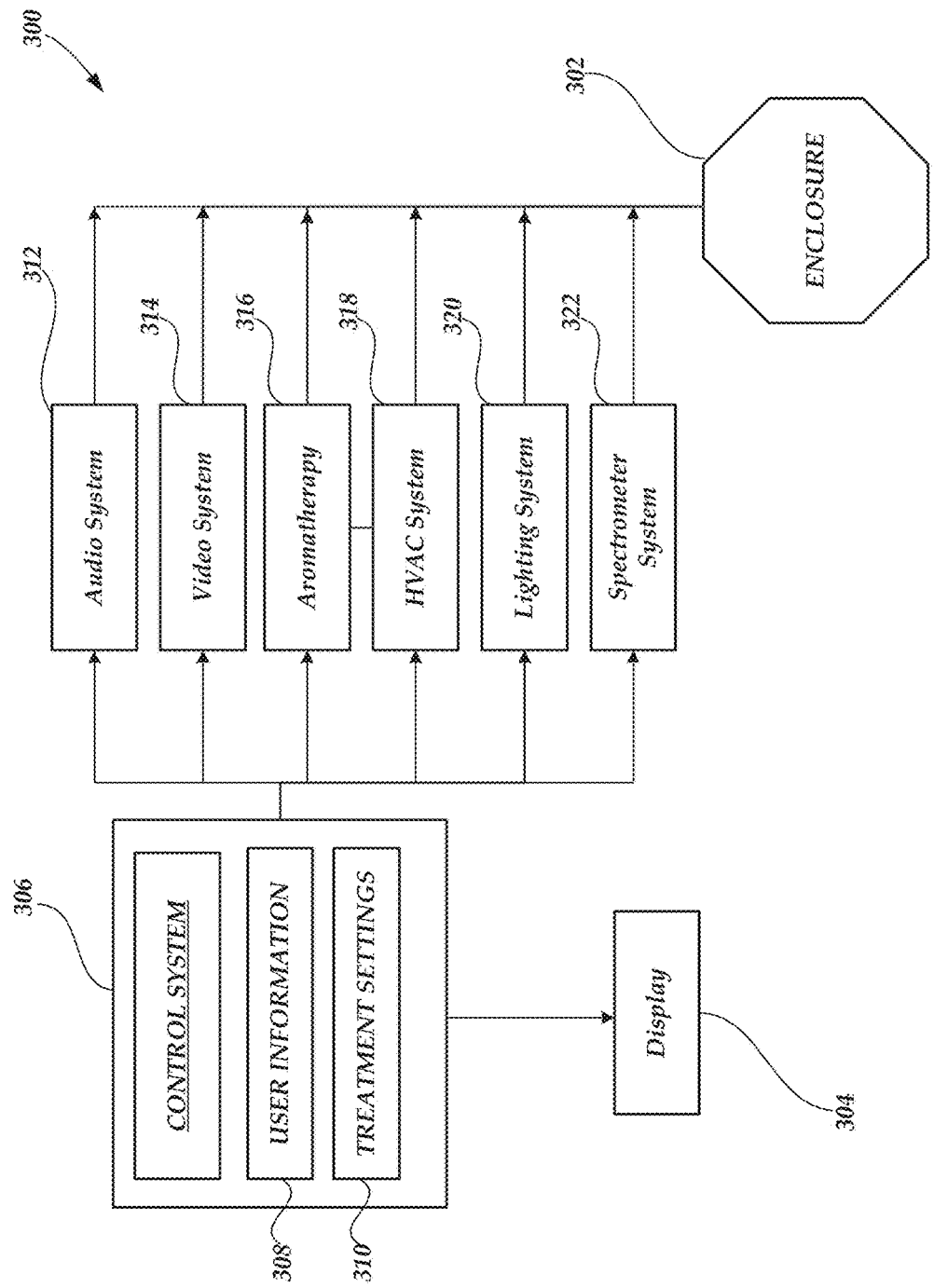
FIG. 3 shows a block diagram illustrating a control system for accessing user information and controlling or selecting one or more settings for therapy, according to the invention.

As described above, methods of providing light therapy may involve regulating one or more therapy settings of enclosures 100 or 200 using corresponding control systems 128 or 228. FIG. 3 depicts a block diagram illustrating control system 306 for accessing and inputting user information 308 and controlling therapy settings 310 of enclosure 302. In at least some embodiments, control system 306 is coupled to display 304 and controls one or more of audio system 312, video system 314, aromatherapy system 316, HVAC system 318, lighting system 320, and spectrometer system 322. It will be understood that the enclosure 302 may include other systems (not shown) that are controlled by the control system 306.

Certain embodiments of methods according to the invention will now be described with respect to FIGS. 4A-4E. FIG. 4A illustrates a logical flow diagram generally showing one embodiment of method 400 for providing therapy(s) that promote relaxation and health. In one embodiment, method 400 begins, after a start block, at block 402, where user information is optionally collected prior to a therapy session.

The method next involves, at block 404, generating a plurality of settings for the therapy based on one or more of: collected user information, including measured information or reported information; historical information; or operator selected information. The plurality of settings may be operator configurable and/or selectable. One or more of the plurality of settings is then selected to provide one or more therapies to the user.

Next, the user is introduced to the enclosure and positioned at a location for receiving one or more therapies. At block 406, one or more therapies are provided to the user according to the one or more settings. For example, emitted light may be directed to the location based on the selected one or more settings over one or more periods of time.

When the one or more therapies is completed, post-therapy information that includes one or more of measured and reported information regarding the user is provided at block 408. Based on the post-therapy information, a report regarding the user is generated at block 410. The method 400 may then return to the start block perform other actions. Each of the actions occurring at blocks 402-410 is described below in greater detail with reference to FIGS. 4B-4E.

User information may be collected for generating and selecting one or more therapy setting (see blocks 402, 404 of FIG. 4A) in a variety of ways. For example, FIG. 4B illustrates a logical flow diagram generally showing one embodiment of method 412 for collecting user information, generating a plurality of therapy settings, and selecting one or more of the plurality of therapy settings. As illustrated in the figure, method 412 begins, after a start block, at block 414, where user identification and contact information are provided. In at least some of the various embodiments, user identification information may include, for example, one or more of the user's name, social security identification, driver's license number, insurance coverage, internal therapy and billing codes, blood type, and next-of-kin information. In at least some of the various embodiments, user contact information may include, for example, one or more of the user's home address, work address, primary care physician contact information, telephone number, and email address.

Information regarding the user's physical attributes is measured at block 416 and may include, for example, one or more of the user's height, weight, age, gender, hair color, ethnicity, blood pressure, observed skin and muscle tone, lung capacity, grip strength, reflexes, and the health of the user's teeth. In at least one of the various embodiments, the user's temperature may be taken at an extremity of the user's body, such as a fingertip or a toe. Because stress is known to promote vasoconstriction and relaxation is known to promote vasodilation, body temperature measured at an extremity may be an indicator of the user's stress level. Accordingly, a lower extremity temperature may indicate a high stress level, while an extremity temperature that is closer to normal body temperature (~98.6° F.) may indicate a lower stress level.

User spectrum information is measured using a spectrometer, such as a handheld spectrometer, at block 418. In this aspect of method 412, a spectrometer is used to detect one or more energy spectra, such as heat, light and electrical charge, radiating or reflecting from the user's body as an indication of the user's physiological state. Handheld spectrometers suitable for use in the present method may include, for example, handheld Raman™ spectrometers from BW Tek™ of Newark, Del.

User reported information is provided at block 420 to provide additional insight into the user's stress and health levels. In at least one of the various embodiments, the user provides survey information related to, for example, the user's perceived present or recent stress level, emotional state, any current medications and diagnosed pathologies, recent life events that may be tied to their stress level and emotional state, their diet, level of exercise, use of tobacco, alcohol, or other substances, and family history of mental health, hypertension, heart disease, or any other conditions.

Alternatively or in addition, the operator may report information regarding, for example, the operator's observations of the user, the operator's interactions with the user, any similarities between the user and one or more other users, and the operator's knowledge of, for example, the date, the season, the geographic location of the therapy, the phase of the lunar cycle, and weather conditions, such as sunlight, rain, dark, difficult driving conditions, and barometric pressure, on the day of the therapy.

Method 412 continues to decision block 422 where, based on the measured user physical attributes, the measured user spectrum values, and the user reported conditions from blocks 416-420, a determination is made as to whether a therapy recommendation regarding one or more therapy settings is appropriate. In at least one of the various embodiments, a therapy recommendation may be made as to one or more therapy settings including, for example: the intensity, type, duration, and cycling of light therapy to be provided to the user; the selection, duration, and volume of an audio therapy to be provided to the user; the selection, duration, and intensity of an aromatherapy to be provided to the user; and the temperature, humidity, ventilation, ionization, filtration, oxygenation, and duration of an air therapy to be provided to the user.

If the operator determines that a therapy recommendation is appropriate, historical information is provided. The historical information may include or more of: heuristic information for a plurality of other users that received one or more therapies; or heuristic information regarding one or more therapies previously received by the user. Heuristic information for a plurality of other users that received therapy and, if applicable, for the user, is provided at block 424. Recommended heuristic therapy settings (block 424) may include one or more of heuristically determined therapy settings based on the user's therapy history or heuristically determined therapy settings values based on the therapy history of a plurality of other users that received therapy. The historical information may also include the user's previous therapy settings, if applicable. The user's previous therapy settings are provided at block 426.

If the operator no therapy recommendations are provided, default therapy settings are provided at block 428. Presented with the therapy settings from one or both of blocks 424 and 426 or, alternatively, block 428, the operator selects one or more of the plurality of settings to provide one or more therapies to the user. One or more of the selected therapy settings may be further configured by the operator. The method 412 may then return to the start block to perform other actions.

Figure 4C:
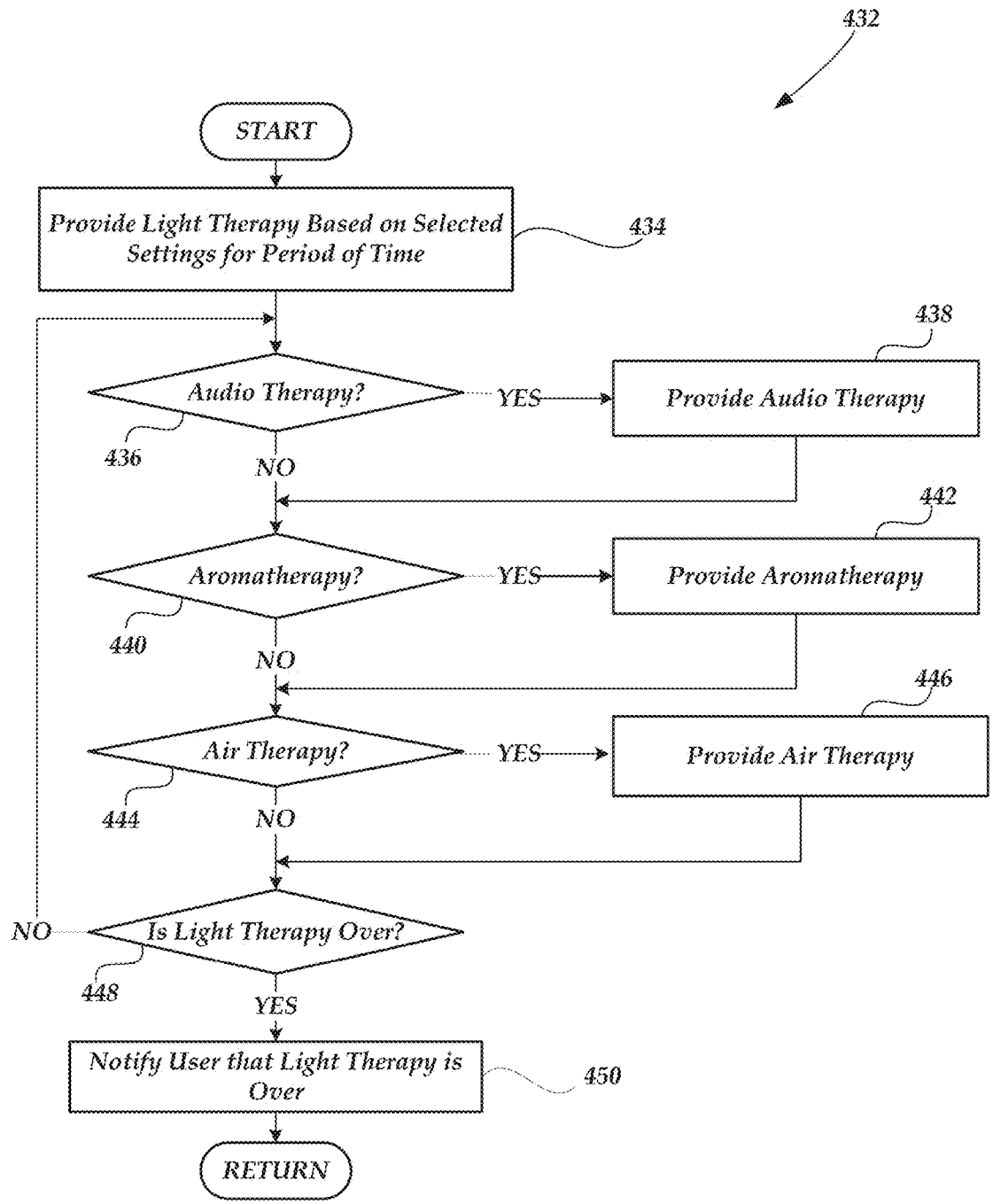
FIG. 4C illustrates a logical flow diagram generally showing one embodiment of a method for providing a light therapy and, optionally, one or more other therapies to a user, according to the invention.
Figure 4D:
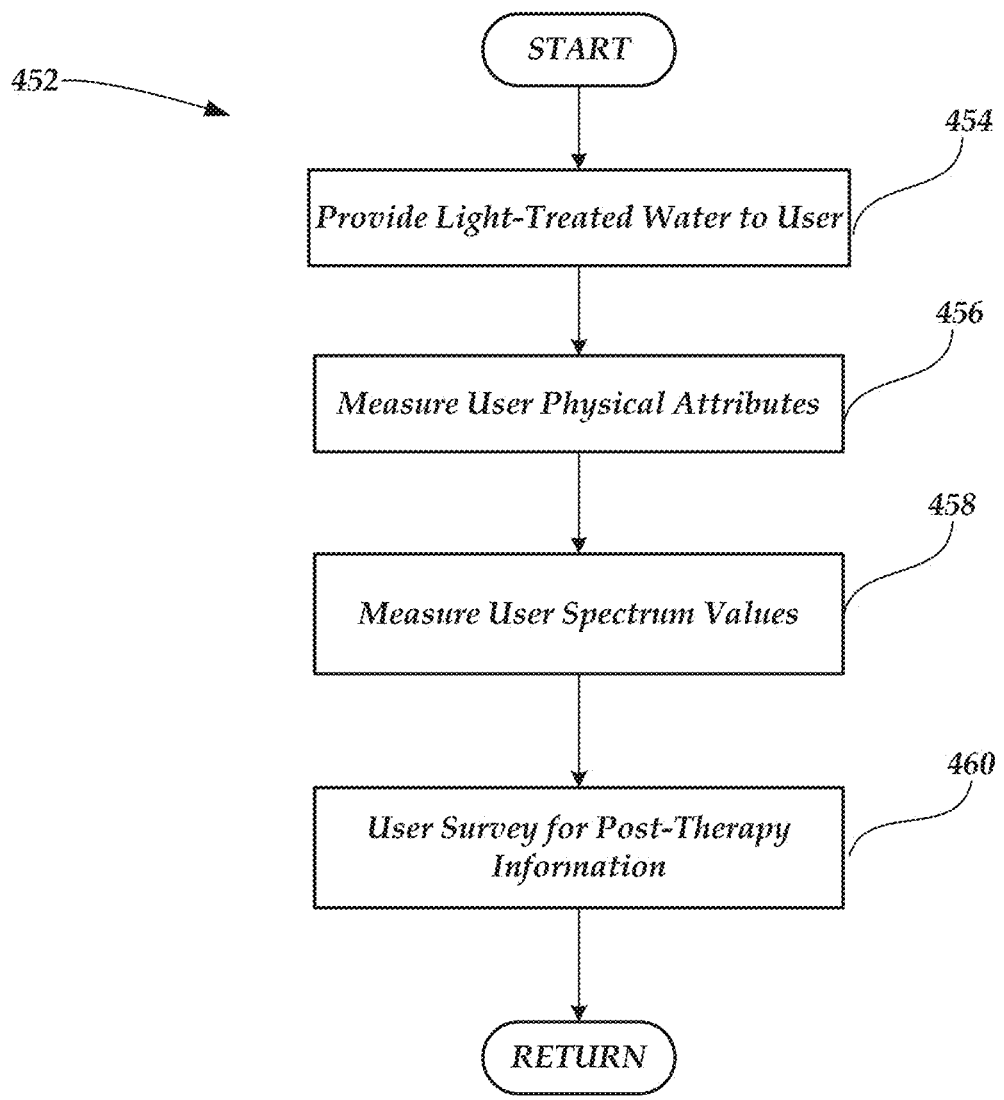
FIG. 4D illustrates a logical flow diagram generally showing one embodiment of a method for completing a therapy session for a user and providing post-therapy user information, according to the invention.

FIG. 4C illustrates a logical flow diagram generally showing one embodiment of a method 432 for providing therapy to a user, according to the invention. After a start block, method 432 begins by providing light therapy to the user in an enclosure according to the invention, such as an enclosure 100, 200, described previously. The light therapy is provided to the user based on the one or more selected therapy settings (see FIG. 4B and foregoing description) for one or more periods of time.

Method 432 continues to decision blocks 436, 440 and 444, where determinations are made, respectively, as to whether an audio therapy, an aromatherapy, or an air therapy is to be provided to the user. It will be understood that the determinations made at decision blocks 436, 440, and 444 may be made in any order.

If it is determined that an audio therapy is to be provided, the audio therapy is provided to the user at block 438 by employing one or more audio therapy sources, over one or more periods of time, to emit one or more audio signals inside the enclosure based on the selected one or more settings. If it is determined an aromatherapy is to be provided, the aromatherapy is provided to the user at block 442 by employing one or more aromatherapy sources, over one or more periods of time, to emit one or more aromas inside the enclosure based on the selected one or more settings. If it is determined that an air therapy is to be provided, air therapy is provided to the user at block 446 by employing one or HVAC devices, over one or more periods of time, to condition the air inside the enclosure based on the selected one or more settings.

Following the determination of whether to provide one or more of an audio therapy, an aromatherapy, or an air therapy, method 432 continues to decision block 448, where a determination is made as to whether the light therapy is over by reference to the selected one or more therapy setting (block 430 in FIG. 4B). If the light therapy is determined not to be over, method 432 returns to repeat decision blocks 436, 440, 444 and to provide one or more of therapies 438, 442, 446, if appropriate, until the light therapy is over. When it is determined that the light therapy is over, method 432 proceeds to block 450, where a notification, such as, for example, an audio notification as previously described, is provided to notify the user that the light therapy is over. Method 432 then returns to the start block to perform other functions.

Additionally, although not shown, the operator may choose to not provide light therapy to a user, and may instead provide one or more of the other therapies, such as audio therapy, aroma therapy, or air therapy to the user within the enclosure.

After the light therapy is complete, the user is removed from the enclosure and further actions may be performed. FIG. 4D illustrates a logical flow diagram generally showing one embodiment of method 452 for providing post-therapy protocols. After a start block, method 452 begins at block 454 by providing a container of water that has been treated by the light therapy to the user to drink. It is known that treatment with UV light may be used to sterilize drinking water by killing bacteria and viruses therein, and it is additionally believed that treating water with light can rearrange the hydrogen and oxygen atoms comprising water molecules to create an ordered and charge-separated ("exclusion zone") arrangement of $H_3O_2$ molecules that, when ingested, are beneficial for smooth functioning of cellular processes.

Post-therapy information regarding the user is provided at blocks 456-460 and includes one or more of measured and reported information. Measured information may include the user's physical attributes, such as, for example, the user's extremity temperature, blood pressure, heart rate, or the user's spectrum values. Reported information may include user survey information regarding, for example, improved feelings of relaxation or alertness, residual stress or pain, feelings of happiness or optimism, or feelings of fatigue or depression. Reported information may additionally or alternatively include information regarding the operator's observations of and interactions with the user. Method 452 may further include collecting one or more of the reported information or the survey information. Method 452 then returns to provide future post-therapy protocols.

Figure 4E:
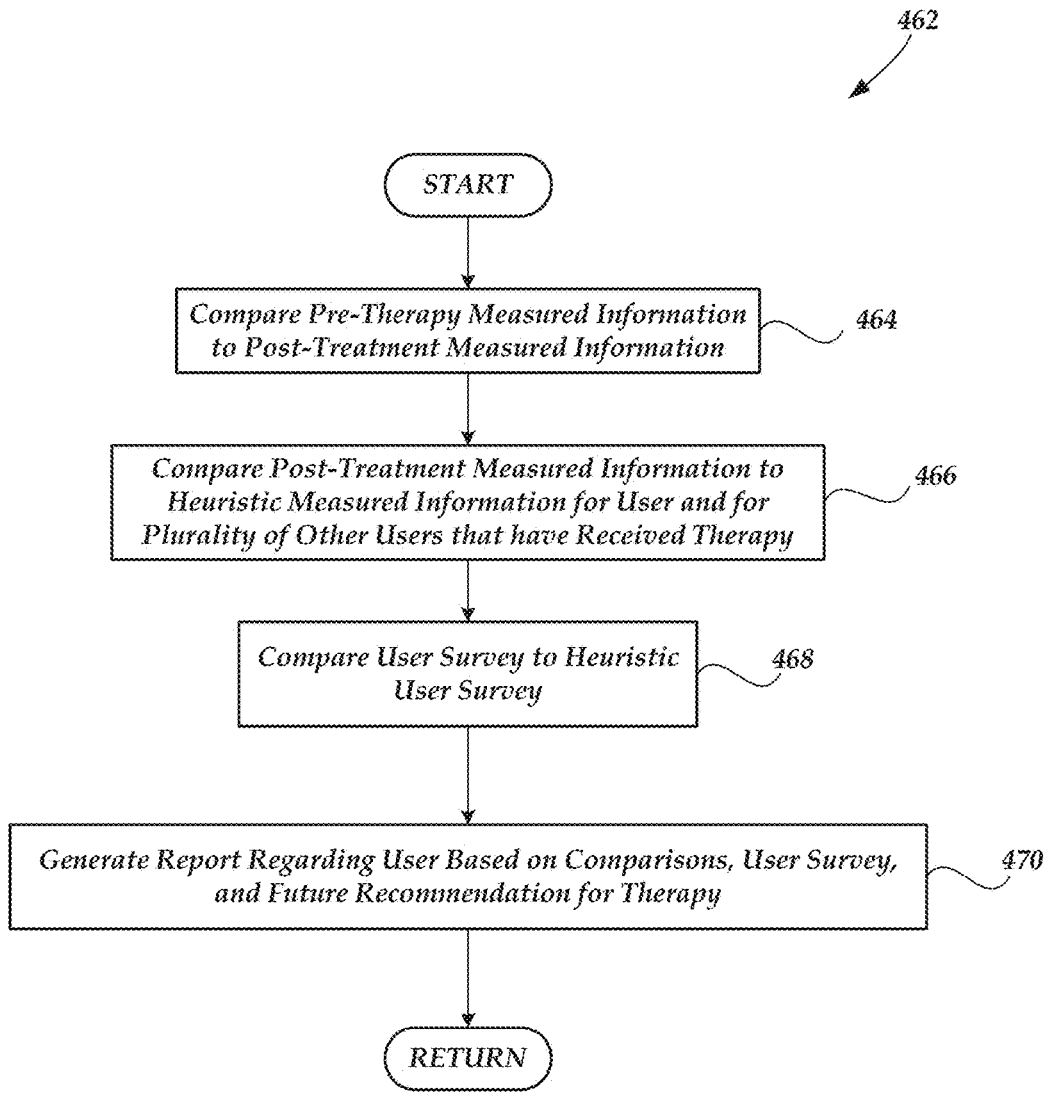
FIG. 4E illustrates a logical flow diagram generally showing one embodiment of a method for generating a report regarding the user based on user information, according to the invention.

The post-therapy information is then used to generate a report regarding the user. FIG. 4E illustrates a logical flow diagram generally showing one embodiment of a method 462 for generating a report regarding the user, according to the invention. After a start block, method 462 begins at block 464, where the user's pre-therapy measured information (blocks 416-420 in FIG. 4B) and post-therapy measured information are compared (blocks 456-460 in FIG. 4D). The user's post-therapy measured values are also compared to heuristic measured values for the user (if applicable) and a plurality of other users that have received therapy at block 466.

Similarly, the user's pre-therapy and post-therapy surveys for the current therapy are compared to a corresponding heuristic user survey (if applicable) at block 468. At block 470, method 462 involves analyzing the comparisons made in blocks 464, 466, and 468 to determine the effects of the current therapy settings on the user. Based on at least this analysis, a report is generated regarding the one or more therapies provided to the user. The report may include or inform a future recommendation to continue the one or more therapies along current settings, to modify one or more of the therapies, or to discontinue one or more of the therapies.

Figure 5A:
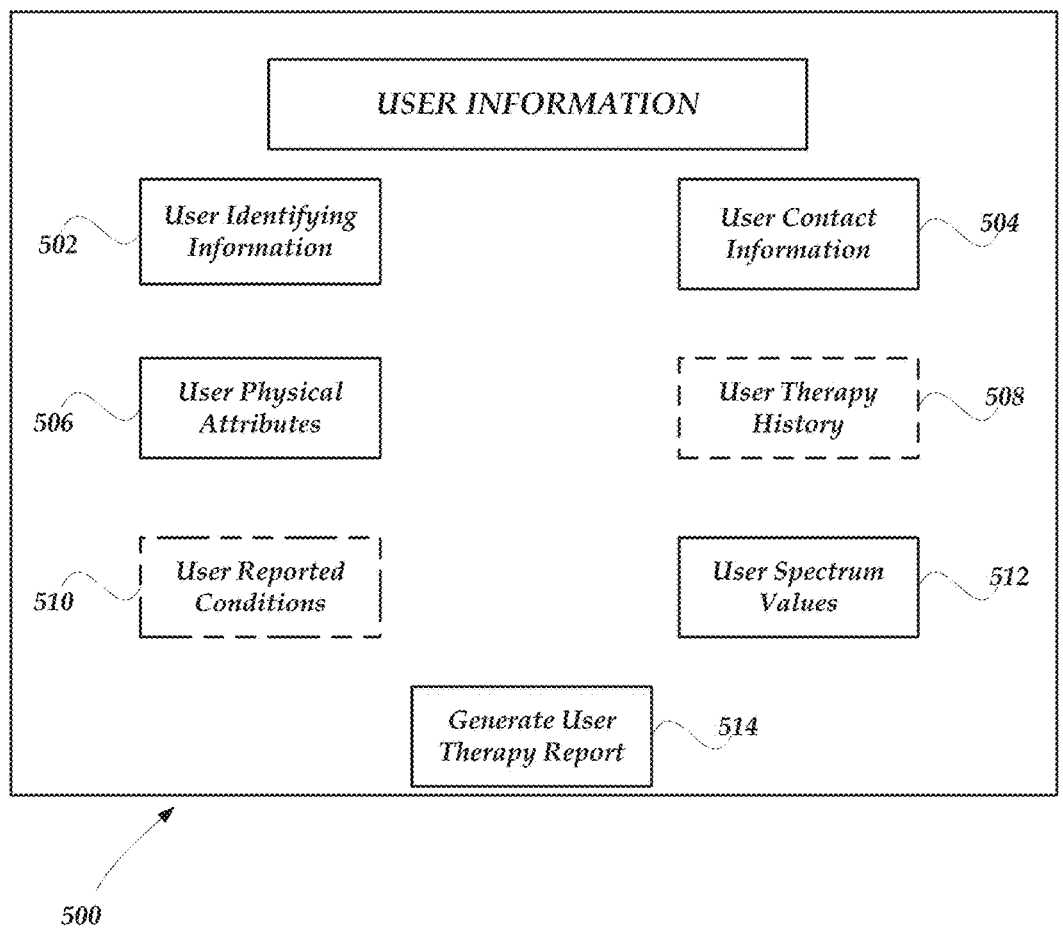
FIG. 5A shows an example of one embodiment of an operator interface for a control system for inputting and accessing user information and generating report regarding the user, according to the invention.

The report may be generated and displayed by an interface that includes one or more of: an analysis of the current therapy(s) provided to the user; an analysis of the previous therapy(s) provided to the user; or a comparative analysis of therapy(s) provided to the user and other users that previously received therapy(s). FIG. 5A shows an exemplary embodiment of interface 500, according to the invention. As shown in the figure, interface 500 permits the operator to access or input user information. For example, the operator may access existing information or input new information regarding the user identifying information 502, user contact information 504, user physical attributes 506, user therapy history 508 (if applicable), user reported conditions 510 (if applicable), and user spectrum values 512 obtained from a spectrometer (not shown), and may generate a report regarding the user.

Figure 5B:
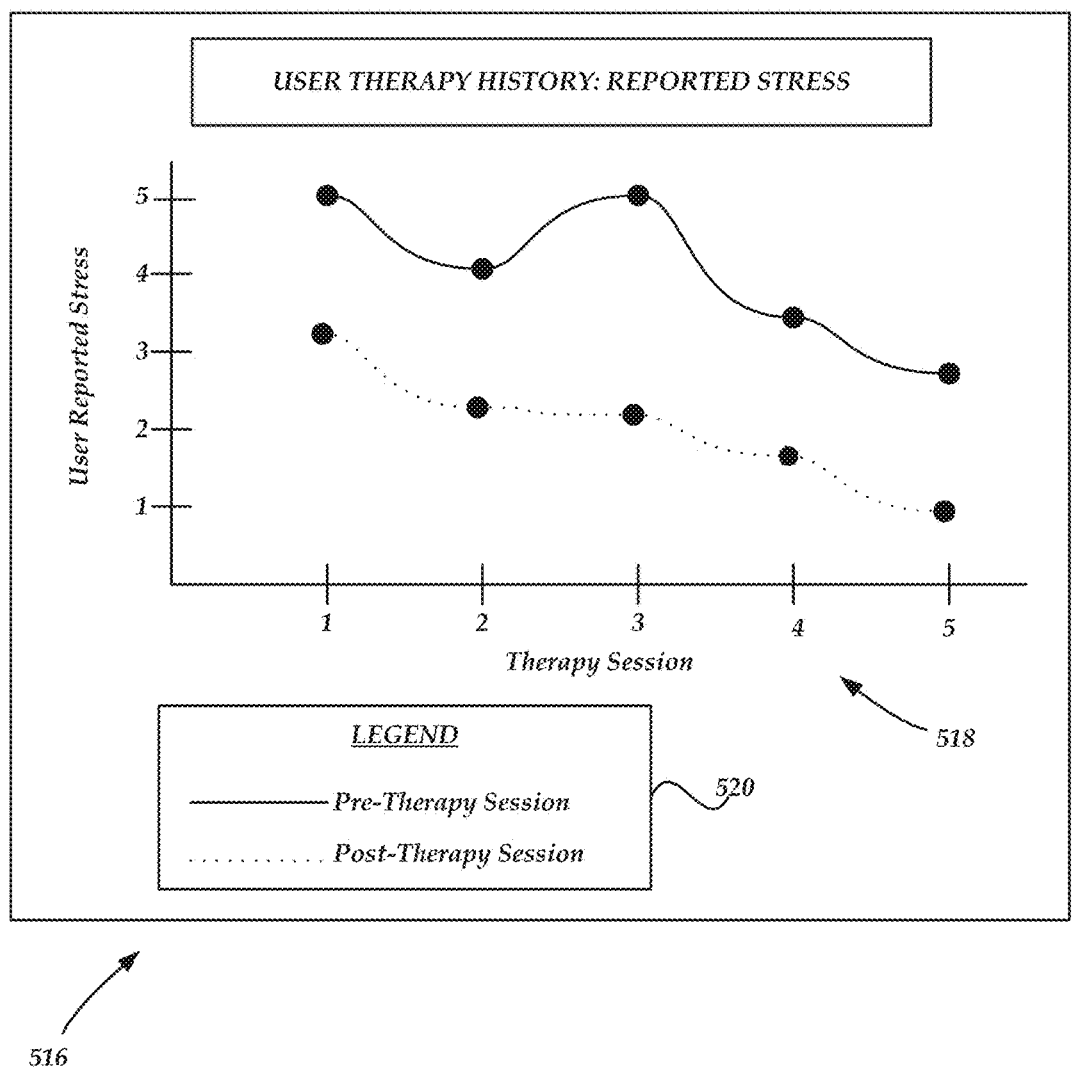
FIG. 5B shows an example of one embodiment of a user interface for a control system for evaluating a user's therapy based on the user reported stress level over a series of therapy sessions, according to the invention.
Figure 5C:
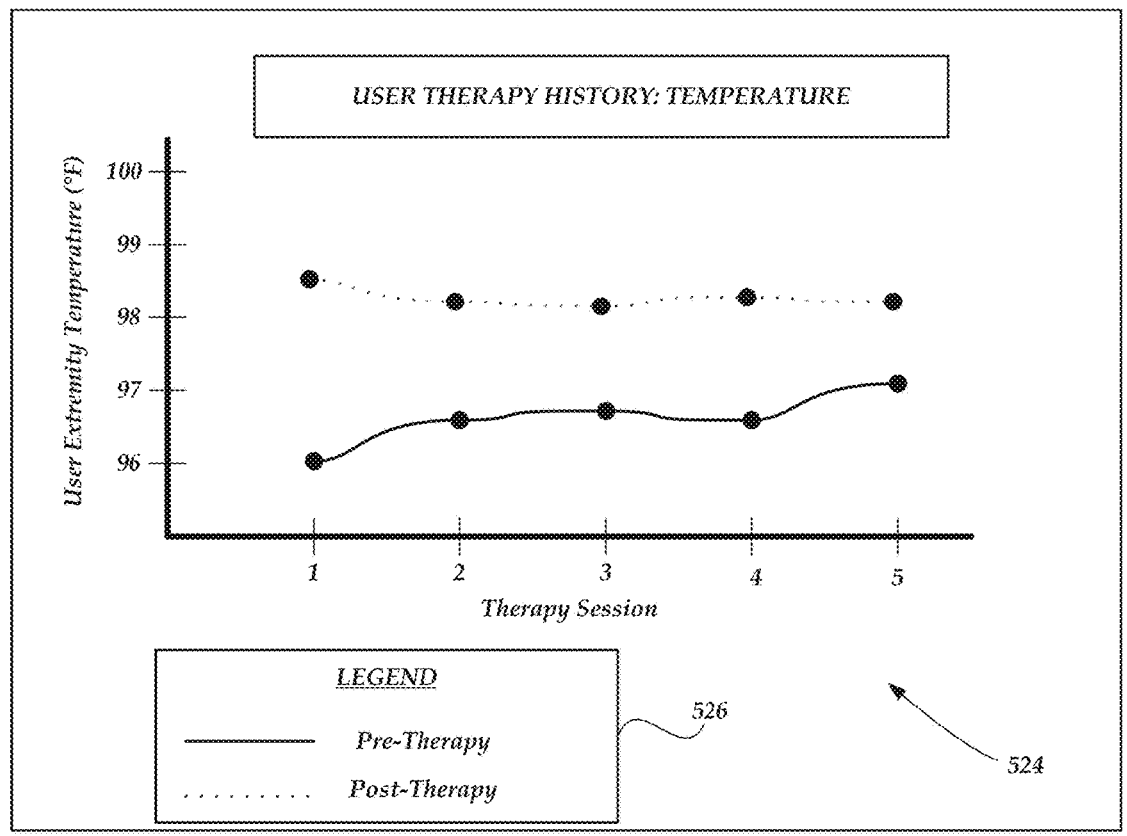
FIG. 5C shows an example of one embodiment of a user interface for a control system for evaluating a user's therapy history based on the temperature of a body extremity of a user over a series of therapy sessions, according to the invention.

FIG. 5B shows one exemplary embodiment of interface 516 for accessing user therapy history. As shown in the figure, interface 516 permits the operator to view a stress metric, such as the user's reported stress level, at pre- and post-therapy reporting periods over a series of therapy sessions at graph 518. Legend 520 assists the operator in interpreting the user therapy history metric information. An exemplary embodiment of interface 522 is shown in FIG. 5C, wherein an operator may access and interpret another stress metric, such as the user's body temperature as measured at an extremity, over a series of therapy sessions in graph 524 with assistance from legend 526.

Figure 5D:
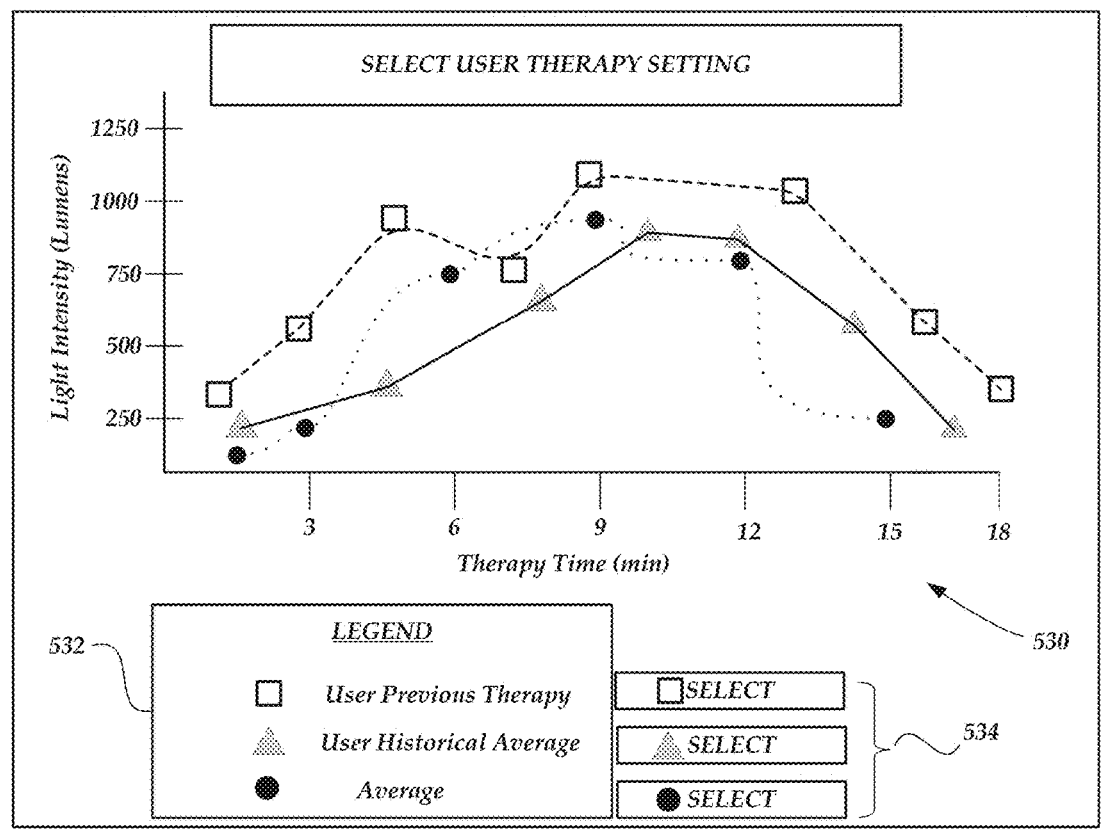
FIG. 5D shows an example of one embodiment of a user interface of a control system for selecting a user therapy setting based on previous therapy settings, according to the invention.

Yet another exemplary embodiment of interface 528 is illustrated in FIG. 5D, wherein an operator may select a recommended therapy setting, such as a light intensity setting over course of a therapy session, by comparing the user's previous therapy setting, the user's historical average therapy setting, and an average therapy setting for a plurality of other users that have received therapy, at graph 530, with reference to legend 532. Once an appropriate therapy recommendation has been determined, the recommended one or more settings for the user therapy may be selected using the corresponding interface tabs 534.

Figure 5E:
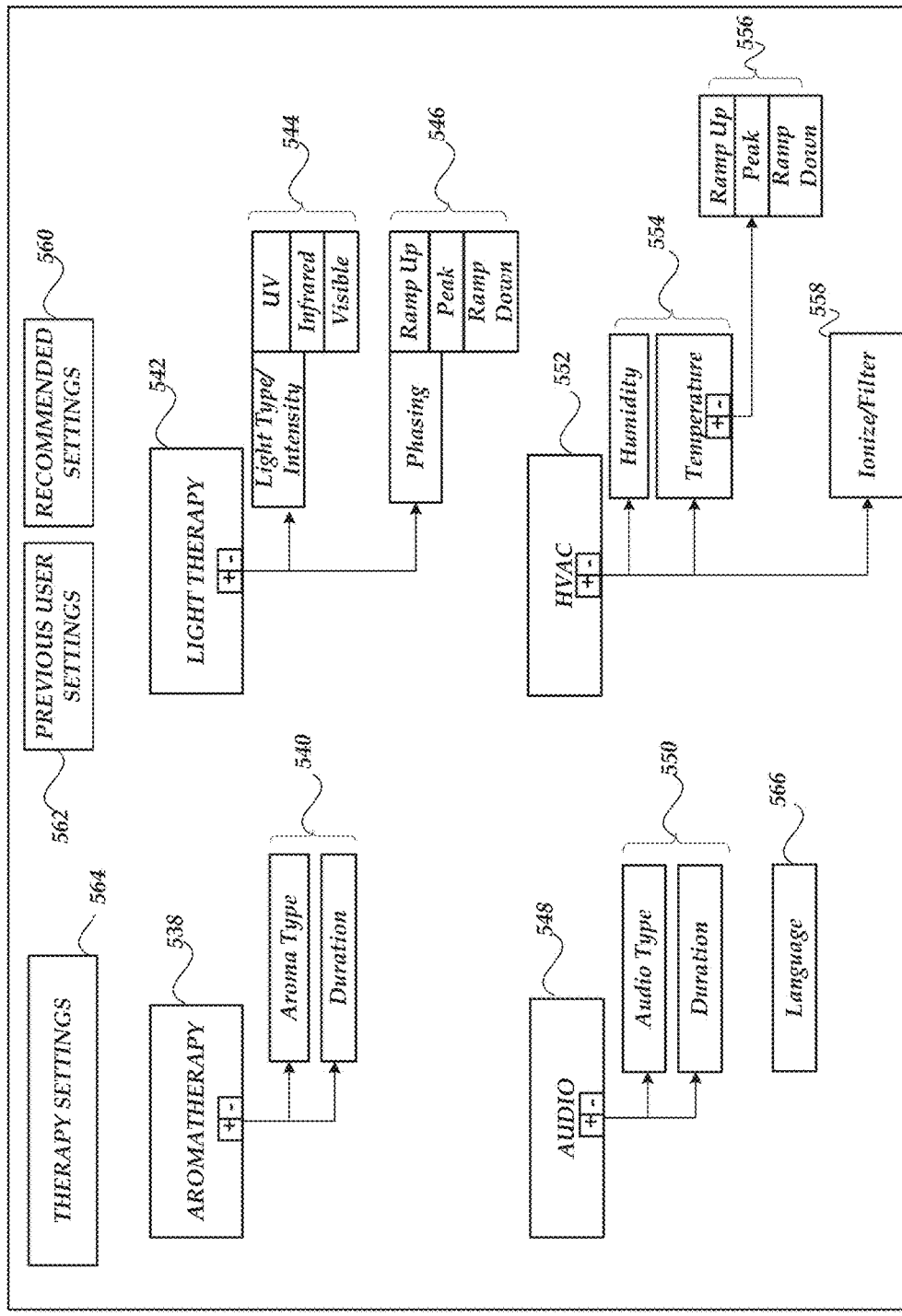
FIG. 5E shows an example of one embodiment of an operator interface for a control system for selecting one or more therapy settings, according to the invention.

Another exemplary embodiment of interface 536 is illustrated in FIG. 5E, wherein an operator may select one or more therapy settings 564. Aroma therapy tab 538 provides access to view or input one or more settings 540 related to aroma type or duration. Light therapy tab 542 provides access to view or input one or more settings related to light type and intensity 544 or phasing 546. Audio tab 548 provides access to view or input one or more settings 550 related to audio type or duration. HVAC tab 552 provides access to view or input one or more settings related to humidity, or temperature 554, such as ramp up, peak, and ramp down settings 556, or one or more settings related to treatment 558 of the air, such as ionization, oxygenation, or filtration. Language tab 566 permits the operator to localize a report by selecting a written language for generating the report regarding the user, based on the relevant language of the one or more of the operator or the user. Also, although not shown, a unit of measurement tab enables the operator to localize a report by selecting a unit of measure for generating the report regarding the user, based on the relevant unit of measurement used at that location, e.g., kilograms/meters versus pounds/feet.

Alternatively, the operator may select either recommended settings 560, such as heuristic settings based on the user or on a plurality of other users who have received therapy, or the user's previous therapy settings 562. It will be appreciated that the interfaces illustrated in FIGS. 5A-5E are for exemplary purposes only, and that a user interface according to the invention may differ from the exemplary embodiments in one or more aspects.

Figure 6:
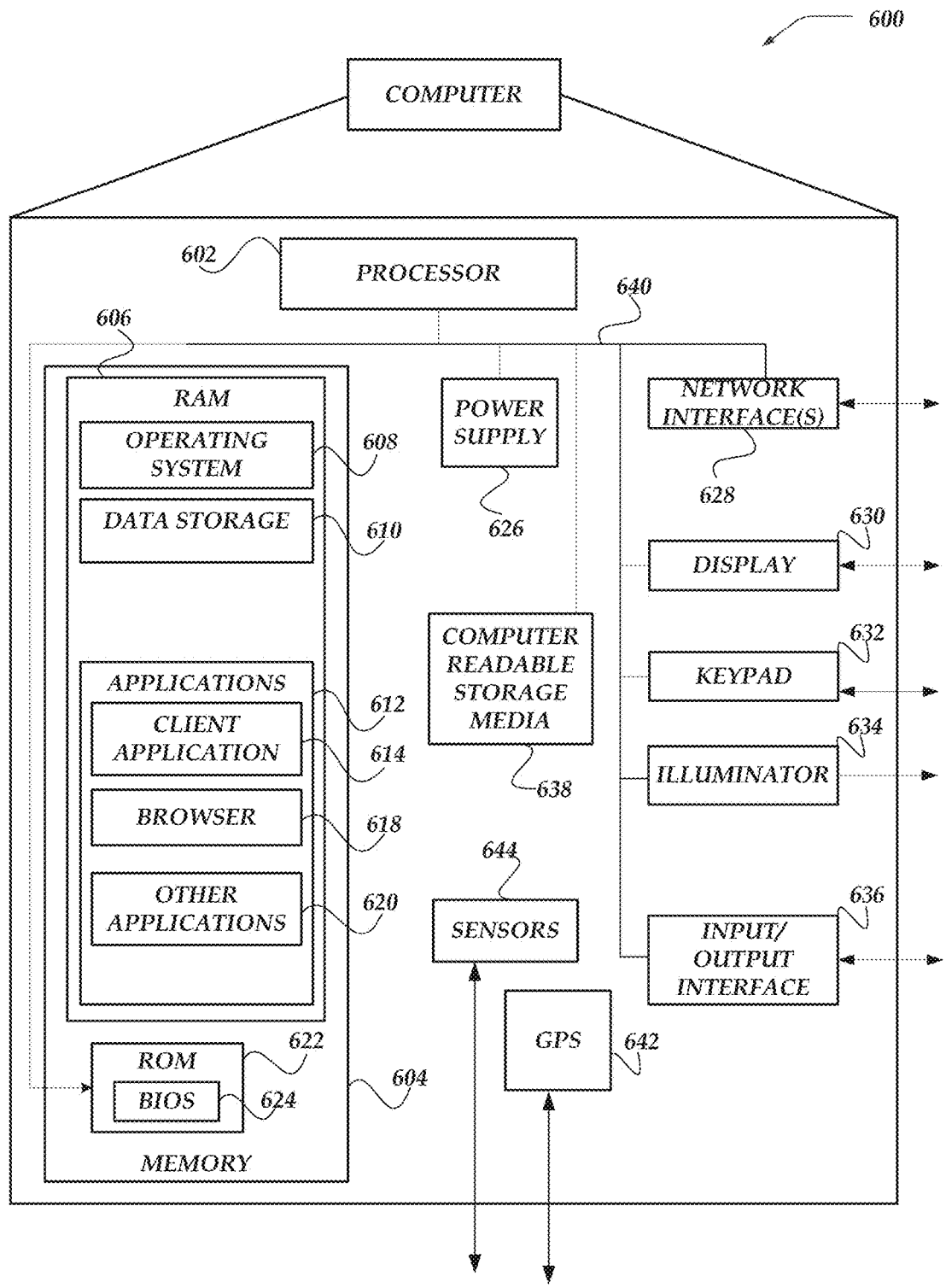
FIG. 6 shows an example of one embodiment of a computer with a computer readable non-transitory storage media that includes instructions for providing therapy to a user positioned within an enclosure, according to the invention.

The invention further includes a computer readable non-transitory storage media that includes instructions for providing therapy to a user positioned within an enclosure according to the invention. The instructions are executed by a computer, such as, for example, computer 600 in FIG. 6, which includes, among other things, processor 602, mass memory 604, and computer readable non-transitory storage media 638. Computer 600 may include many more or less components than those shown in FIG. 6.

As shown in the figure, computer 600 includes processor 602 in communication with mass memory 604 via bus 640. In some embodiments, processor 602 may include one or more central processing units (CPU), or logical circuitry such as an ASIC. Computer 600 also includes power supply 626, one or more network interfaces 628, display 630, keypad 632, illuminator 634, and input/output interface 636.

Mass memory 604 includes Random Access Memory (RAM) 606, Read-only Memory (ROM) 622, and other storage means. Mass memory 604 illustrates an example of computer readable transitory and non-transitory storage media (devices) for storage of information such as computer readable instructions, data structures, program modules or other data. Mass memory 602 stores basic input/output system (BIOS) 624, or the like, for controlling low-level operation of computer 600. The mass memory also stores an operating system 608 for controlling the operation of computer 600. It will be appreciated that this component may include a general-purpose operating system such as a version of UNIX, or LINUX™, or a specialized client communication operating system such as Microsoft Corporation's Windows Mobile™, Apple Corporation's iOS™, Google Corporation's Android™ or the Symbian® operating system, or the like. The operating system may include, or interface with a Java virtual machine module, or the like, that enables control of hardware components and/or operating system operations via application programs.

Mass memory 604 further includes one or more data storage 610, which can be utilized by computer 600 to store, among other things, applications 612, such as a given client application 614, browser 618, or other applications 620 and/or other data. For example, data storage 610 may also be employed to store information that describes various capabilities of computer 600. The information may then be provided to another computer based on any of a variety of events, including being sent as part of a header during a communication, sent upon request, or the like.

Computer 600 may optionally communicate with a base station (not shown), or directly with another computer. Network interface 628 includes circuitry for coupling computer 600 to one or more networks, and is constructed for use with one or more wired or wireless communication protocols and technologies including, but not limited to, GSM, CDMA, TDMA, GPRS, EDGE, WCDMA, HSDP A, LTE, user datagram protocol (UDP), transmission control protocol/Internet protocol (TCP/IP), short message service (SMS), WAP, ultra wide band (UWB), IEEE 802.16 Worldwide Interoperability for Microwave Access (WiMax), session initiated protocol/real-time transport protocol (SIP/RTP), or any of a variety of other wireless communication protocols. Network interface 628 is sometimes known as a transceiver, transceiving device, or network interface card (NIC).

Display 630 may be liquid crystal display (LCD), gas, plasma, LED, organic LED, or any other type of display used with a computer. Display 630 may also include a touch sensitive screen arranged to receive input from an object such as a stylus or a digit from a human hand.

Keypad 632 may comprise any input device arranged to receive input from an operator. For example, keypad 632 may include a push button numeric dial, or a keyboard. Keypad 632 may also include command buttons that are associated with selecting and sending images.

Illuminator 634 may provide a status indication and/or provide light. Illuminator 634 may remain active for specific periods of time or in response to events. For example, when illuminator 634 is active, it may backlight the buttons on keypad 634 and stay on while the computer is powered. Also, illuminator 634 may backlight these buttons in various patterns when particular actions are performed, such as dialing another computer. Illuminator 634 may also cause light sources positioned within a transparent or translucent case of the computer to illuminate in response to actions.

Computer readable storage media 638 may include volatile, non-transitory, non-transitive, nonvolatile, removable, and non-removable media implemented in any method or technology for storage of information, such as computer or processor-readable instructions, data structures, program modules, or other data. Examples of computer readable storage media include RAM, ROM, Electrically Erasable Programmable Read-only Memory (EEPROM), flash memory or other memory technology, Compact Disc Read-only Memory (CD-ROM), digital versatile disks (DVD) 5 or other optical storage, solid state drives (SSD), magnetic cassettes, magnetic tape, magnetic disk storage or other magnetic storage devices, or any other physical medium which can be used to store the desired information and which can be accessed by a computer.

The computer 600 may further include GPS transceiver 642 to determine the physical coordinates of computer 600 and, by extension, a location of the apparatus on the surface of the Earth. GPS transceiver 642, in some embodiments, may be optional. GPS transceiver 642 typically outputs a location as latitude and longitude values. However, GPS transceiver 642 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of computer 600 and, by extension, the apparatus, on the surface of the Earth. In one of the various embodiments, GPS transceiver 642 may be used to localize the language and the units of measure to a physical region associated with a specific written language, thereby automatically calibrating, for example, the report regarding the user to be reported in the relevant written language and units of measure for a user or operator physically located in that region. In one of the various embodiments, a language setting may be configurable by the operator (see 566 in FIG. 5E) to override an automatic GPS based localization when, for example, the operator is familiar with another language and other units of measure that are different from those associated with the physical region.

It is understood that under different conditions, GPS transceiver 642 can determine a physical location within millimeters for computer 600; and in other cases, the determined physical location may be less precise, such as within a meter or significantly greater differences. In one embodiment, however, computer 600 may, through other components, provide other information that may be employed to determine a physical location of the computer, including, for example, a Media Access Control (MAC) address, IP address, or the like.

The computer 600 may also include sensors 644 for determining geolocation information (e.g., GPS), determining timing (e.g., the hour, day, month, and year of the therapy session in the given time zone), monitoring electrical power conditions (e.g., voltage sensors, current sensors, frequency sensors, and so on), monitoring weather (e.g., thermostats, barometers, anemometers, humidity detectors, precipitation scales), or the like.

In one example, the sensors may use the barometric pressure around the enclosure to determine, for example, an altitude or changing weather at the physical location of the enclosure. In another example, the sensor information may be used to determine that, based on the latitudinal position of the apparatus, diurnal cycles may be shorter or longer on the date of therapy than they might be at another latitudinal position. Accordingly, the light therapy settings may be set to mimic the current diurnal cycle specific to the localized physical region where the enclosure is located. Similarly, localization information determined by the sensors may determine that the apparatus is located in a region prone to extreme weather events, such as monsoons, that may affect ambient temperature, humidity, and other phenomena, in which case, one or more settings related to air therapy, such as temperature, humidity, or air treatment may be adjusted.

The sensed information may be used to automatically adjust one or more therapy settings to compensate for the changes, or may be used to alert the operator that an adjustment may be necessary. In one example, the sensed information may be used to evaluate or predict the stress or health-related symptoms of the user, and likely causes thereof, based on known aspects of the given geographic region, such as heat, humidity, altitude, amount of sunlight, length of a diurnal cycle, proximity to magnetic lines, lunar cycle, and the like for the specific location, and to automatically adjust one or more therapy settings appropriately. In another example, the sensed information is provided to the operator in an alert, which the operator can choose to react to or ignore. Sensors 644 may be one or more hardware sensors that collect and/or measure data that is external to computer 600.

Execution of the instructions by the computer 600 provides actions, including: generating a plurality of settings for the therapy based on one or more of: measured information, reported information, historical information, or operator selected information; selecting one or more of the plurality of settings to provide therapy to the user, wherein the one or more settings are operator configurable; positioning the user at a location within the enclosure, wherein a floor, a ceiling and each wall of the enclosure are configured to focus light at the location when light is provided by plurality of light sources, and wherein the plurality of light sources is located at one or more of the floor, the ceiling, or one or more walls of the enclosure.

The actions further include: providing therapy to the user by employing the plurality of light sources, over one or more periods of time, to emit light directed to the location based on the selected one or more settings; providing post-therapy information that includes one or more of measured and reported information regarding the user; and generating a report regarding the user based on the post-therapy information, wherein the report includes analysis of the therapy provided to the user.

What is claimed as new and desired to be protected by Letters Patent of the United States is:

1. A method for providing therapy to a user positioned within an enclosure, comprising:
   generating a plurality of settings for the therapy based on one or more of: measured information, reported information, historical information, or operator selected information;
   selecting one or more of the plurality of settings to provide therapy to the user, wherein the one or more settings are operator configurable;
   positioning the user at a location within the enclosure, wherein the enclosure comprises a plurality of walls arranged in an octagonal shape with a diameter of approximately nine feet to focus light at the location when light is provided by a plurality of directly emitting light sources, and wherein the plurality of directly emitting light sources are located equidistant from the location at four or more positions on separate walk of the enclosure to directly emit light to form a three-dimensional region of maximum light density at the location and also achieve resonance of the directly emitted light at the location;
   providing therapy to the user by employing the plurality of light sources, over one or more periods of time, to emit light directly onto the user positioned in the three-dimensional region at the location based on the selected one or more settings, wherein the maximum light density and the resonance of the directly emitted light occur at the location to promote the effectiveness of the therapy for the user;
   providing post-therapy information that includes one or more of measured and reported information regarding the user; and
   generating a report regarding the user based on the post-therapy information.

2. The method of claim 1, wherein when the one or more of measured information regarding the user is included in the post-therapy information, the measured information regarding the user includes one or more of:
   measured physical attributes of the user; or
   spectrum values of the user collected by a spectrometer.

3. The method of claim 1, further comprising one or more of:
   collecting reported information provided by one or more of the user or the operator; or
   collecting survey information provided by the user.

4. The method of claim 1, wherein when generating the plurality of settings for the therapy is based on the historical information, the historical information includes one or more of:
   heuristic information for a plurality of other users that received therapy; or
   heuristic information regarding therapy previously received by the user.

5. The method of claim 1, wherein the selected one or more settings include one or more of: ramp up, ramp down, plateau, intensity up, intensity down, type of light source, type of audio source, type of aroma, amount of aroma, air temperature, air humidity, air ionization, air filtration, or time period.

6. The method of claim 1, further comprising providing one or more additional therapies, including:
   aromatherapy to the user by employing one or more aromatherapy sources, over one or more periods of time, to emit one or more aromas inside the enclosure based on the selected one or more settings;

audio therapy to the user by employing one or more audio therapy sources, over one or more periods of time, to emit one or more audio signals inside the enclosure based on the selected one or more settings; or air therapy to the user by employing one or more heating ventilation and air conditioning (HVAC) devices, over one or more periods of time, to condition the air inside the enclosure based on the selected one or more settings.

7. The method of claim 1, further comprising:
providing a container of water in the enclosure; and
providing the water to the user for drinking after the therapy is provided to the user.

8. The method of claim 1, wherein the report is displayed in a user interface and the displayed report includes one or more of:
an analysis of the current therapy provided to the user;
an analysis of previous therapy provided to the user;
a comparative analysis of therapy provided to the user and other users that previously received therapy.

9. The method of claim 1, further comprising:
employing one or more sensors to collect information regarding an environment around the enclosure; and
automatically adjusting one or more therapies provided to the user based on the environment information, wherein the one or more therapies include light therapy, aroma therapy, heating ventilation and air conditioning (HVAC) therapy, or audio therapy.

10. An apparatus for providing therapy to a user positioned at a location within an enclosure, comprising:
the enclosure, wherein the enclosure comprises a plurality of walls arranged in an octagonal shape with a diameter of approximately nine feet to focus light at the location when light is provided by a plurality of directly emitting light sources, wherein the plurality of directly emitting light sources are located equidistant from the location at four or more positions on separate walls of the enclosure to directly emit light to form a three-dimensional region of maximum light density at the location and also achieve resonance of the directly emitted light at the location; and
a control system, including:
a memory that stores instructions; and
a processor that is configured to execute the instructions to perform a method, the method comprising:
generating a plurality of settings for the therapy based on one or more of: measured information, reported information, historical information, or operator selected information;
selecting one or more of the plurality of settings to provide therapy to the user, wherein the one or more settings are operator configurable;
providing therapy to the user by employing the plurality of light sources, over one or more periods of time, to emit light directly onto the user positioned in the three-dimensional region at the location based on the selected one or more settings, wherein the maximum light density and the resonance of the directly emitted light occur at the location to promote the effectiveness of the therapy for the user;
providing post-therapy information that includes one or more of measured and reported information regarding, the user; and
generating a report regarding the user based on the post-therapy information, wherein the report includes analysis of the therapy provided to the user; and a display that presents the report to one or more of the operator and the user.

11. The apparatus of claim 10, wherein when the one or more of measured information regarding the user is included in the post-therapy information, the measured information regarding the user includes one or more of:
measured physical attributes of the user; or
spectrum values of the user collected by a spectrometer.

12. The apparatus of claim 10, further comprising a reflective surface attached to one or more of the ceiling, the floor, or one or more walls.

13. The apparatus of claim 10, wherein the enclosure is configured as one of: a fixed structure, a portable structure, or a temporary structure that is configured for assembly and disassembly in one or more remote locations.

14. The apparatus of claim 10, wherein the selected one or more settings include one or more of: ramp up, ramp down, plateau, intensity up, intensity down, type of light source, type of audio source, type of aroma, amount of aroma, air temperature, air humidity, air ionization, air filtration, or time period.

15. The apparatus of claim 10, further comprising providing one or more additional therapies, including:
aromatherapy to the user by employing one or more aromatherapy sources, over one or more periods of time, to emit one or more aromas inside the enclosure based on the selected one or more settings;
audio therapy to the user by employing one or more audio therapy sources, over one or more periods of time, to emit one or more audio signals inside the enclosure based on the selected one or more settings; or
air therapy to the user by employing one or more heating ventilation and air conditioning (HVAC) devices, over one or more periods of time, to condition the air inside the enclosure based on the selected one or more settings.

16. The apparatus of claim 10, further comprising a global positioning system (GPS), transceiver that is employed to detect a location of the apparatus, wherein the location is employed by the control system to localize the spoken language that is used for one or more of the measured information, reported information, historical information, operator selected information, plurality of settings, selected settings, or the report.

17. The apparatus of claim 10, wherein the report is displayed by the display in a user interface and the displayed report includes one or more of:
an analysis of the current therapy provided to the user;
an analysis of previous therapy provided to the user;
a comparative analysis of therapy provided to the user and other users that previously received therapy.

18. The apparatus of claim 10, wherein the enclosure further comprises a diameter of nine feet.

19. The apparatus of claim 10, further comprising:
employing one or more sensors to collect information regarding an environment around the enclosure; and
automatically adjusting one or more therapies provided to the user based on the environment information, wherein the one or more therapies include light therapy, aroma therapy, heating ventilation and air conditioning (HVAC) therapy, or audio therapy.

20. A computer readable non-transitory storage media that includes instructions for providing therapy to a user positioned at a location within an enclosure, wherein execution of the instructions by a computer performs a method comprising:

generating a plurality of settings for the therapy based on one or more of: measured information, reported information, historical information, or operator selected information;
selecting one or more of the plurality of settings to provide therapy to the user, wherein the one or more settings are operator configurable for the enclosure, wherein the enclosure comprises a plurality of walls arranged in an octagonal shape with a diameter of approximately nine feet to focus light at the location when light is provided by a plurality of directly emitting light sources, and wherein the plurality of directly emitting light sources are located equidistant from the location at four or more positions on separate walls of the enclosure to directly emit light to form a three-dimensional region of maximum light density at the location and also achieve resonance of the directly emitted light at the location;
providing therapy to the user by employing the plurality of light sources, over one or more periods of time, to emit light directly onto the user positioned in the three-dimensional region at the location based on the selected one or more settings, wherein the maximum light density and the resonance of the directly emitted light occur at the location to promote the effectiveness of the therapy for the user;
providing post-therapy information that includes one or more of measured and reported information regarding the user; and
generating a report regarding the user based on the post-therapy information, wherein the report includes analysis of the therapy provided to the user.

* * * * *